(12) United States Patent
Traverse et al.

(10) Patent No.: US 9,975,872 B2
(45) Date of Patent: May 22, 2018

(54) PROCESSES FOR THE PREPARATION OF (S)-3-(4-((4-(MORPHOLINOMETHYL) BENZYL)OXY)-1-OXOISOINDOLIN-2-YL) PIPERIDINE-2,6-DIONE AND PHARMACEUTICALLY ACCEPTABLE FORMS THEREOF

(71) Applicant: Celgene Corporation, Summit, NJ (US)

(72) Inventors: John F. Traverse, Roselle Park, NJ (US); Chengmin Zhang, Florham Park, NJ (US); Gregg B. Feigelson, Chester, NY (US); Benjamin M. Cohen, Cranford, NJ (US); William W. Leong, Westfield, NJ (US)

(73) Assignee: Celgene Corporation, Summit, NJ (US)

( * ) Notice: Subject to any disclaimer, the term of this patent is extended or adjusted under 35 U.S.C. 154(b) by 0 days. days.

(21) Appl. No.: 15/058,976

(22) Filed: Mar. 2, 2016

(65) Prior Publication Data

US 2016/0251333 A1 Sep. 1, 2016

Related U.S. Application Data

(63) Continuation of application No. 13/962,764, filed on Aug. 8, 2013, now Pat. No. 9,309,220.

(60) Provisional application No. 61/681,477, filed on Aug. 9, 2012.

(51) Int. Cl.
*C07D 401/04* (2006.01)
*C07D 413/14* (2006.01)

(52) U.S. Cl.
CPC ......... *C07D 401/04* (2013.01); *C07D 413/14* (2013.01)

(58) Field of Classification Search
CPC ............................. C07D 401/04; C07D 413/14
USPC .......................................................... 544/130
See application file for complete search history.

(56) References Cited

U.S. PATENT DOCUMENTS

| | | | |
|---|---|---|---|
| 2006/0160854 A1* | 7/2006 | Muller | C07D 401/04 514/323 |
| 2011/0196150 A1* | 8/2011 | Man | C07D 401/04 540/544 |

FOREIGN PATENT DOCUMENTS

| | | |
|---|---|---|
| WO | 2006/028964 A1 | 3/2006 |
| WO | 2007/005972 A1 | 1/2007 |
| WO | 2008/115516 A2 | 9/2008 |
| WO | 2011/100380 A1 | 8/2011 |
| WO | 2011/111053 A1 | 9/2011 |
| WO | 2013/126394 A1 | 8/2013 |

OTHER PUBLICATIONS

Wang, Y., and A. Chen "Enantioenrichment by Crystallization" Org. Proc. Res. Dev. (2008), 12: pp. 282-290.*
Silva et al., "Synthesis of N-[(3S)-2,6-Dioxo-1-(2-phenylethyl)-3-piperidinyl]-(2S)-2-methylbutanamide ((-)-Julocrotine)," J. Nat. Prod., 74:1531-1534 (2011).
Wang et al., "Eutectic Composition of a Chiral Mixture Containing a Racemic Compound," Org. Proc. Res. Dev., 9:670-676 (2005).
Wang et al., "Enantioenrichment by Crystallization," Org. Proc. Res. Dev., 12:282-290 (2008).

* cited by examiner

*Primary Examiner* — Matthew P Coughlin
*Assistant Examiner* — Sagar Patel
(74) *Attorney, Agent, or Firm* — Jones Day

(57) ABSTRACT

Provided are processes for the preparation of enantiomerically enriched or enantiomerically pure 3-(4-((4-(morpholinomethyl)benzyl)oxy)-1-oxoisoindolin-2-yl)piperidine-2,6-dione, or a pharmaceutically acceptable form thereof.

12 Claims, 5 Drawing Sheets

EUTECTIC SOLUBILITY OF THE HCL
SALT OF (S)-3-(4-((4-(MORPHOLINOMETHYL)BENZYL)OXY)-
1-OXOISOINDOLIN-2-YL)PIPERIDINE-2,6-DIONE AS A FUNCTION
OF TEMPERATURE IN VARIOUS SOLVENT SYSTEMS

PROCESSES FOR THE PREPARATION OF (S)-3-(4-((4-(MORPHOLINOMETHYL) BENZYL)OXY)-1-OXOISOINDOLIN-2-YL) PIPERIDINE-2,6-DIONE AND PHARMACEUTICALLY ACCEPTABLE FORMS THEREOF

1. CLAIM OF PRIORITY

The present application is a continuation application of U.S. patent application Ser. No. 13/962,764, filed on Aug. 8, 2013, which claims priority to U.S. Provisional Application No. 61/681,477, filed Aug. 9, 2012, the entirety of each of which is incorporated herein by reference.

2. FIELD

Provided herein are processes for the preparation of enantiomerically enriched or enantiomerically pure 3-(4-((4-(morpholinomethyl)benzyl)oxy)-1-oxoisoindolin-2-yl)piperidine-2,6-dione, or a pharmaceutically acceptable form thereof, which is useful for treating, preventing and managing various disorders.

3. BACKGROUND

Many types of cancers are associated with new blood vessel formation, a process known as angiogenesis. Several of the mechanisms involved in tumor-induced angiogenesis have been elucidated. The most direct of these mechanisms is the secretion by the tumor cells of cytokines with angiogenic properties, including tumor necrosis factor α (TNF-α).

A variety of other diseases and disorders are also associated with, or characterized by, undesired angiogenesis. For example, enhanced or unregulated angiogenesis has been implicated in a number of diseases and medical conditions including, but not limited to, ocular neovascular diseases, choroidal neovascular diseases, retina neovascular diseases, rubeosis (neovascularization of the angle), viral diseases, genetic diseases, inflammatory diseases, allergic diseases, and autoimmune diseases. Examples of such diseases and conditions include, but are not limited to: diabetic retinopathy; retinopathy of prematurity; corneal graft rejection; neovascular glaucoma; retrolental fibroplasia; arthritis; and proliferative vitreoretinopathy.

Certain 4'-arylmethoxy isoindoline compounds, including 3-(4-((4-(morpholinomethyl)benzyl)oxy)-1-oxoisoindolin-2-yl)piperidine-2,6-dione, have been reported to be capable of controlling angiogenesis or inhibiting the production of certain cytokines, including TNF-α, and useful in the treatment and prevention of various diseases and conditions. See U.S. Patent Publication No. 2011/0196150, which is incorporated herein by reference in its entirety.

Methods for synthesizing racemic 3-(4-((4-(morpholinomethyl)benzyl)oxy)-1-oxoisoindolin-2-yl)piperidine-2,6-dione have been previously described in U.S. Patent Publication No. 2011/0196150. A need still exists for efficient and scalable processes for the preparation of enantiomerically enriched or enantiomerically pure 3-(4-((4-(morpholinomethyl)benzyl)oxy)-1-oxoisoindolin-2-yl)piperidine-2,6-dione, or a pharmaceutically acceptable form thereof.

Among general approaches for providing enantiomerically enriched or enantiomerically pure compounds, utilizing naturally or commercially available enantiopure starting materials is the most straightforward approach and is often preferred for processes of industrial scale. One of the challenges often encountered by this approach is full or partial racemization during the synthetic process, which leads to decrease of the enantiomeric excess (ee) of the material. In order to minimize the chance of racemization, harsh reaction conditions are often avoided wherever possible.

In addition to the need for synthetic processes for the preparation of an enantiomerically enriched or enantiomerically pure compound, a need for a method that can increase the enantiopurity of a compound still exists, because process deviations can result in lower ee even if the process is capable of providing the compound with a high ee. Further, developing a method that can increase the product ee may allow for alternative synthetic routes to the enantiomerically enriched or enantiomerically pure compound, resulting in lower cost of goods and a more streamlined manufacturing process.

General methods for ee enhancement by crystallization based on the thermodynamic relationship between racemic mixture and enantiopure species have been reported (Wang et al., *Org. Proc. Res. Dev.*, 2005, 9, 670; Wang et al., *Org. Proc. Res. Dev.*, 2008, 12, 282; Jacques, J.; Collet, A.; Wilen, S. H. *Enatniomers, Racemates and Resolution*; John Wiley & Sons: New York, 1981). Development of a crystallization method for a direct ee enhancement typically includes three steps: (1) determining the thermodynamically stable phase of the racemate (conglomerate, racemic compound, or pseudoracemate) at the temperature of interest, (2) obtaining the key solubility data, and (3) designing the crystallization process.

The majority of racemic mixtures preferentially form racemic compounds (reference Jacques book). The saturation solubility of a racemic compound and the pure enantiomer in the presence of a solvent is known as the eutectic point. The ratio of the solubility, i.e., the "eutectic enantioexcess" ($ee_{eu}$), is a useful parameter to assess the chiral upgrade capability for a given system. The $ee_{eu}$ is calculated from the relative solubility of the R- and S-enantiomers: $ee_{eu}=([major]-[minor])/([major]+[minor])$, where [major] is the solubility of the major enantiomer at the eutectic, and [minor] is the solubility of the minor enantiomer at the eutectic. Provided that the most stable crystalline forms of the racemic compound and single enantiomer are used, in dilute solutions, the $ee_{eu}$ should be independent of solvent selection, unless one or both of the forms are solvates and/or the solvent under study is chiral. The $ee_{eu}$ can be dependent on temperature in all cases.

In the case of racemic compound, low $ee_{eu}$ is desired to increase ee of a compound in the solids. This occurs when the racemic compound has relatively high solubility compared to the single enantiomer. In the case of a low $ee_{eu}$, facile purification can occur by a trituration or recrystallization of the crude mixture in a specified solvent, followed by filtration, which will afford enantiomerically enriched or enantiomerically pure solids with a mixture of both enantiomers dissolved in the filtrate.

Identifying a low $ee_{eu}$ condition often requires extensive solubility screening of a range of crystalline forms, solvents and conditions, and in many cases still cannot be achieved.

4. SUMMARY

Provided herein are processes for the preparation of an enantiomerically enriched or enantiomerically pure compound of Formula (I):

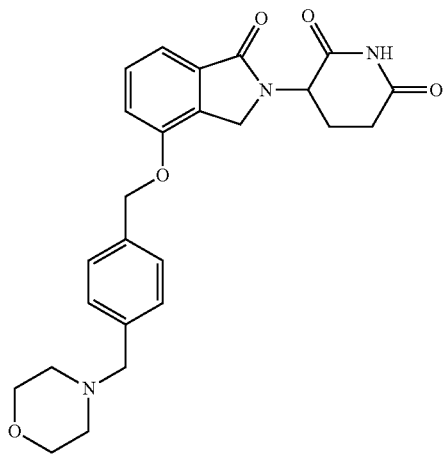

(I)

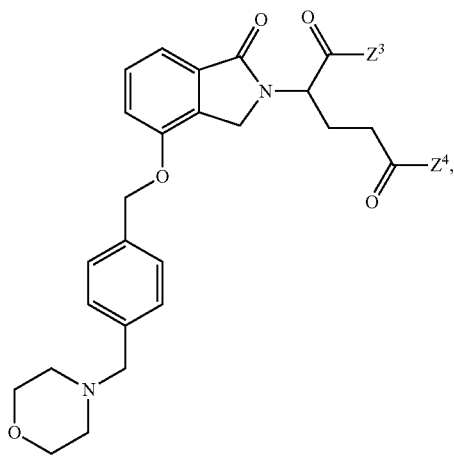

(III)

or a pharmaceutically acceptable form thereof. A compound of Formula (I) has the chemical name of 3-(4-((4-(morpholinomethyl)benzyl)oxy)-1-oxoisoindolin-2-yl)piperidine-2,6-dione. In one embodiment, the compound is (S)-3-(4-((4-(morpholinomethyl)benzyl)oxy)-1-oxoisoindolin-2-yl) piperidine-2,6-dione, or a pharmaceutically acceptable form thereof. In one embodiment, the compound is (S)-3-(4-((4-(morpholinomethyl)benzyl)oxy)-1-oxoisoindolin-2-yl)piperidine-2,6-dione hydrochloride, which is also known as (3S)-3-(4-{[4-(morpholin-4-ylmethyl)benzyl]oxy}-1-oxo-1,3-dihydro-2H-isoindol-2-yl)piperidine-2,6-dione hydrochloride (1:1), or 2,6-piperidinedione, 3-[1,3-dihydro-4-[[4-(4-morpholinylmethyl)phenyl]methoxy]-1-oxo-2H-isoindol-2-yl]-, (3S)—, hydrochloride (1:1).

In one embodiment, provided herein are processes for the preparation of an enantiomerically enriched or enantiomerically pure compound of Formula (I), or a pharmaceutically acceptable form thereof, comprising:

(step 1.1) transforming an enantiomerically enriched or enantiomerically pure compound of Formula (II):

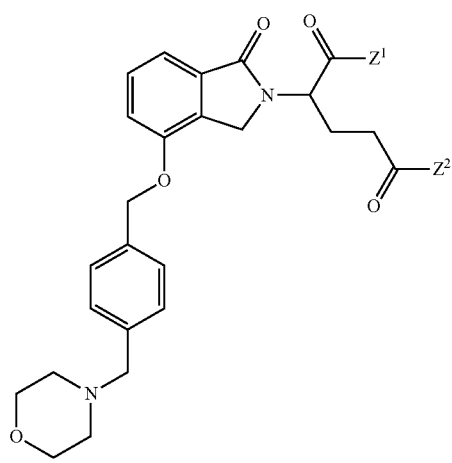

(II)

or a salt thereof, wherein
(i) $Z^1$ is NHY, and $Z^2$ is OR; or
(ii) $Z^1$ is OR, and $Z^2$ is NHY;
wherein R and Y are defined herein elsewhere;
to an enantiomerically enriched or enantiomerically pure compound of Formula (III):

or a salt thereof, wherein
(i) $Z^3$ is NHY, and $Z^4$ is OH; or
(ii) $Z^3$ is OH, and $Z^4$ is NHY;
under conditions suitable for ester to acid transformation;
(step 1.2) cyclizing the enantiomerically enriched or enantiomerically pure compound of Formula (III) to an enantiomerically enriched or enantiomerically pure compound of Formula (I-a):

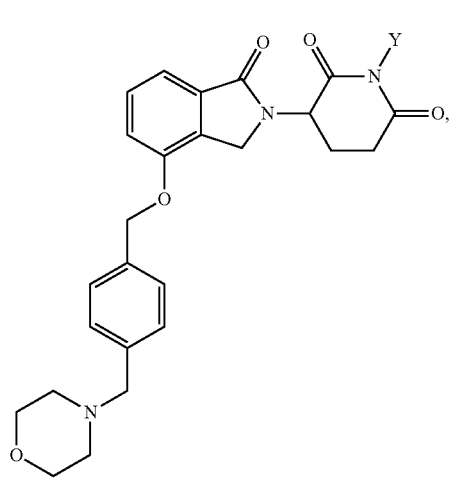

(I-a)

under conditions suitable for cyclization;
(step 1.3) where Y is not hydrogen, deprotecting the enantiomerically enriched or enantiomerically pure compound of Formula (I-a) to an enantiomerically enriched or enantiomerically pure compound of Formula (I) under conditions suitable for deprotection; and
(step 1.4) optionally transforming the enantiomerically enriched or enantiomerically pure compound of Formula (I) to a pharmaceutically acceptable salt thereof under conditions suitable for salt formation.

Also provided herein are methods for increasing the enantiopurity of a compound of Formula (I), or a salt and/or solvate thereof. In one embodiment, without being limited by any particular theory, such methods are based on thermodynamic relationship between (S)- and racemic 3-(4-((4-(morpholinomethyl)benzyl)oxy)-1-oxoisoindolin-2-yl)piperidine-2,6-dione, or a salt and/or solvate thereof.

5. BRIEF DESCRIPTION OF THE FIGURES

6. DETAILED DESCRIPTION

6.1 Definition

Figure 1:
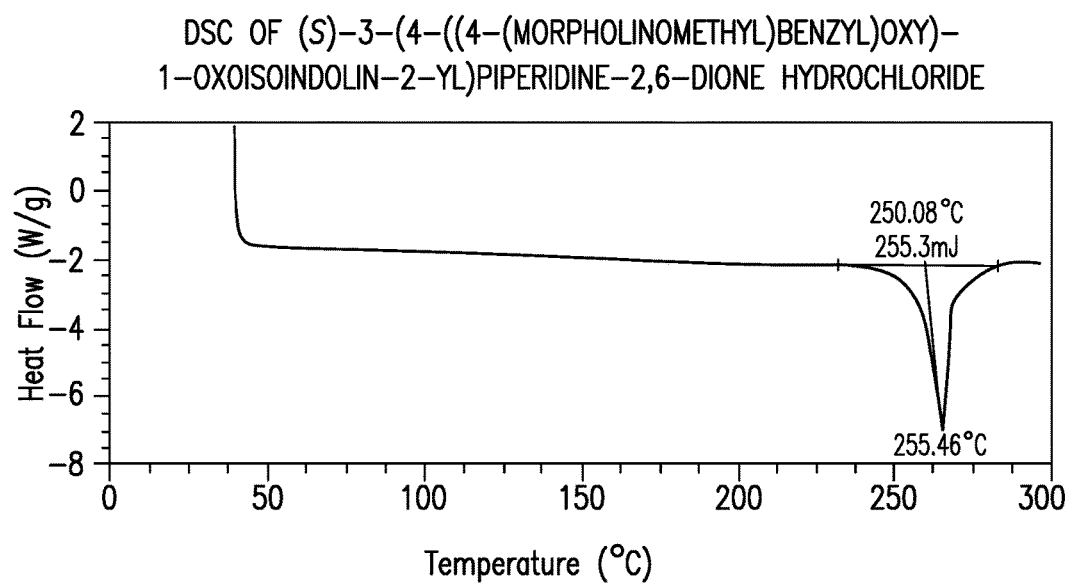
FIG. 1 depicts a differential scanning calorimetric (DSC) thermogram of (S)-3-(4-((4-(morpholinomethyl)benzyl)oxy)-1-oxoisoindolin-2-yl)piperidine-2,6-dione hydrochloride.

As used herein and unless otherwise indicated, the term "process(es)" provided herein refers to the methods disclosed herein which are useful for preparing a compound provided herein. Modifications to the methods disclosed herein (e.g., starting materials, reagents, protecting groups, solvents, temperatures, reaction times, purification) are also encompassed by the present disclosure.

As used herein, and unless otherwise indicated, the term "adding," "reacting," "treating," or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

As used herein, and unless otherwise indicated, the term "transforming" refers to subjecting the compound at hand to reaction conditions suitable to effect the formation of the desired compound at hand.

As used herein, and unless otherwise specified, a "one-pot" process refers to a process of preparing a desired product, wherein all reactants are added simultaneously or successively, and wherein no separation, isolation, and/or purification of any intermediate formed is conducted before the formation of the desired product is substantially complete. A "one-pot" process is preferably conducted in a single container, but may be conducted in more than one container.

As used herein, and unless otherwise indicated, a reaction that is "substantially complete" or is driven to "substantial completion" means that the reaction contains more than about 50% by percent yield, in one embodiment more than about 60% by percent yield, in one embodiment more than about 70% by percent yield, in one embodiment more than about 80% by percent yield, in one embodiment more than about 90% by percent yield, in another embodiment more than about 95% by percent yield, and in another embodiment more than about 97% by percent yield of the desired product.

As used herein, and unless otherwise specified, a "pharmaceutically acceptable form" includes any pharmaceutically acceptable salts, solvates, stereoisomers, polymorphs, or prodrugs of a compound.

As used herein, and unless otherwise indicated, the term "salt" includes, but is not limited to, salts of acidic or basic groups that may be present in the compounds disclosed herein. Compounds that are basic in nature are capable of forming a wide variety of salts with various inorganic and organic acids. The acids that may be used to prepare salts of such basic compounds are those that form salts comprising anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate, methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Compounds that include an amino group also can form salts with various amino acids, in addition to the acids mentioned above. Compounds that are acidic in nature are capable of forming base salts with various cations. Non-limiting examples of such salts include alkali metal or alkaline earth metal salts and, in some embodiments, calcium, magnesium, sodium, lithium, zinc, potassium, and iron salts. Compounds that are acidic in nature are also capable of forming base salts with compounds that include an amino group.

As used herein, and unless otherwise specified, the term "solvate" means a compound that further includes a stoichiometric or non-stoichiometric amount of solvent bound by non-covalent intermolecular forces. Where the solvent is water, the solvate is a hydrate.

As used herein, and unless otherwise specified, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Discovery*, 172-178, 949-982 (Manfred E. Wolff ed., 5th ed. 1995), and *Design of Prodrugs* (H. Bundgaard ed., Elsevier, N.Y. 1985).

As used herein, and unless otherwise specified, the terms "biohydrolyzable carbamate," "biohydrolyzable carbonate," "biohydrolyzable ureide" and "biohydrolyzable phosphate" mean a carbamate, carbonate, ureide and phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable carbamates include, but are not limited to, carbamates that include lower alkylamine, substituted ethylenediamine, aminoacid, hydroxyalkylamine, heterocyclic and heteroaromatic amine, and polyether amine moieties.

As used herein, and unless otherwise specified, the term "stereoisomer" encompasses all enantiomerically/stereomerically pure and enantiomerically/stereomerically enriched compounds provided herein.

If the stereochemistry of a structure or a portion thereof is not indicated, e.g., with bold or dashed lines, the structure or portion thereof is to be interpreted as encompassing all enantiomerically pure, enantiomerically enriched, diastereomerically pure, diastereomerically enriched, and racemic mixtures of the compounds.

Unless otherwise indicated, the terms "enantiomerically enriched" and "enantiomerically pure," as used interchangeably herein, refer to compositions in which the percent by weight of one enantiomer is greater than the amount of that one enantiomer in a control mixture of the racemic composition (e.g., greater than 1:1 by weight). For example, an enantiomerically enriched preparation of the (S)-enantiomer, means a preparation of the compound having greater than 50% by weight of the (S)-enantiomer relative to the (R)-enantiomer, such as at least 75% by weight, and even such as at least 80% by weight. In some embodiments, the enrichment can be much greater than 80% by weight, providing a "substantially optically enriched," "substantially enantiomerically enriched," "substantially enantiomerically pure" or a "substantially non-racemic" preparation, which refers to preparations of compositions which have at least 85% by weight of one enantiomer relative to other enantiomer, such as at least 90% by weight, and such as at least 95% by weight. In some embodiments, the enantiomerically enriched composition has a higher potency with respect to therapeutic utility per unit mass than does the racemic mixture of that composition.

As used herein, and unless otherwise specified, "polymorph" refers to a crystalline compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism, the different crystal types are the result of hydration or solvation.

As used herein, and unless otherwise indicated, the term "halo", "halogen", or the like means —F, —Cl, —Br, or —I.

As used herein, and unless otherwise specified, the term "alkyl" refers to a saturated straight chain or branched hydrocarbon having a number of carbon atoms as specified herein. In some embodiments, alkyl groups have 1 to 15, 1 to 10, 1 to 6, or 1 to 3 carbon atoms. Representative saturated straight chain alkyls include -methyl, -ethyl, -n-propyl, -n-butyl, -n-pentyl, and -n-hexyl; while saturated branched alkyls include -isopropyl, -sec-butyl, -isobutyl, -tert-butyl, -isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The term "alkyl" also encompasses cycloalkyl.

As used herein, and unless otherwise specified, the term "heteroalkyl" refers to an alkyl in which one or more, in some embodiments, 1 to 3, carbon atoms are replaced by heteroatoms such as, but not limited to, N, S, O and Si, and wherein the nitrogen and sulfur atoms may optionally be oxidized and the nitrogen atom may optionally be quaternized. Examples include —$CH_2$—$CH_2$—O—$CH_3$, —$CH_2$—$CH_2$—NH—$CH_3$, —$CH_2$—$CH_2$—N($CH_3$)$_2$, —$CH_2$—S—$CH_2$—$CH_3$, —$CH_2$—$CH_2$—S(O)—$CH_3$, —$CH_2$—$CH_2$—S(O)$_2$—$CH_3$, —Si($CH_3$)$_3$, and —$CH_2$—CH=N—O$CH_3$. Up to two heteroatoms may be consecutive, such as, for example, —$CH_2$—NH—O$CH_3$ and —$CH_2$—O—Si($CH_3$)$_3$. When a prefix such as $C_{2-6}$ is used to refer to a heteroalkyl group, the number of carbons (2-6, in this example) is meant to include the heteroatoms as well. For example, a $C_{2-6}$ heteroalkyl group is meant to include, for example, —$CH_2$OH (one carbon atom and one heteroatom replacing a carbon atom) and —$CH_2$SH. In some embodiments, heteroalkyl groups have 2 to 15, 2 to 10, 2 to 6, or 2 to 3 carbon and hetero atoms As used herein, and unless otherwise specified, the term "cycloalkyl" means a species of alkyl, which is cyclic and contains from 3 to 15, 3 to 9, 3 to 6, or 3 to 5 carbon atoms, without alternating or resonating double bonds between carbon atoms. It may contain from 1 to 4 rings. Examples of unsubstituted cycloalkyls include, but are not limited to, cyclopropyl, cyclobutyl, cyclopentyl, cyclohexyl, and adamantyl. A cycloalkyl may be substituted with one or more substituents. In some embodiments, a cycloalkyl may be a cycloalkyl fused with aryl or heteroaryl groups.

As used herein, and unless otherwise specified, the term "heterocycloalkyl" means a cycloalkyl in which one or more, in some embodiments, 1 to 3, carbon atoms are replaced by heteroatoms such as, but not limited to, N, S, and O. In some embodiments, a heterocycloalkyl group contains from 3 to 15, 3 to 9, 3 to 6, or 3 to 5 carbon and hetero atoms. In some embodiments, a heterocycloalkyl may be a heterocycloalkyl fused with aryl or heteroaryl groups. When a prefix such as $C_{3-6}$ is used to refer to a heterocycloalkyl group, the number of carbons (3-6, in this example) is meant to include the heteroatoms as well. For example, a $C_{3-6}$ heterocycloalkyl group is meant to include, for example, tetrahydropyranyl (five carbon atoms and one heteroatom replacing a carbon atom).

As used herein, and unless otherwise specified, the term "aryl" means a carbocyclic aromatic ring containing from 5 to 14 ring atoms. The ring atoms of a carbocyclic aryl group are all carbon atoms. Aryl ring structures include compounds having one or more ring structures such as mono-, bi-, or tricyclic compounds as well as benzo-fused carbocyclic moieties such as 5,6,7,8-tetrahydronaphthyl and the like. Specifically, the aryl group may be a mono-, bi-, or tricyclic ring. Representative aryl groups include phenyl, anthracenyl, fluorenyl, indenyl, azulenyl, phenanthrenyl and naphthyl.

As used herein, and unless otherwise specified, the term "heteroaryl" refers to a monocyclic or multicyclic aromatic ring system, in certain embodiments, of about 5 to about 15 members where one or more, in some embodiments, 1 to 3, of the atoms in the ring system is a heteroatom, that is, an element other than carbon, including but not limited to, N, O or S. The heteroaryl group may be optionally fused to a benzene ring. Heteroaryl groups include, but are not limited to, furyl, imidazolyl, indolinyl, pyrrolidinyl, pyrimidinyl, tetrazolyl, thienyl, pyridyl, pyrrolyl, N-methylpyrrolyl, quinolinyl and isoquinolinyl.

As used herein, and unless otherwise specified, the term "aralkyl" refers to an alkyl group in which one of the hydrogen atoms of the alkyl is replaced by an aryl group.

Where the number of any given substituent is not specified (e.g., "haloalkyl"), there may be one or more substituents present. For example, "haloalkyl" may include one or more of the same or different halogens.

As used herein, and unless otherwise indicated, the term "alcohol" means any compound substituted with an —OH group.

As used herein, and unless otherwise indicated, the term "amino" or "amino group" means a monovalent group of the formula —NH$_2$, —NH(alkyl), —NH(aryl), —N(alkyl)$_2$, —N(aryl)$_2$ or —N(alkyl)(aryl).

Unless otherwise indicated, the compounds provided herein, including intermediates useful for the preparation of the compounds provided herein, which contain reactive functional groups (such as, without limitation, carboxy, hydroxy, and amino moieties) also include protected derivatives thereof. "Protected derivatives" are those compounds in which a reactive site or sites are blocked with one or more protecting groups (also known as blocking groups). Suitable protecting groups are well known to those of ordinary skill in the art. The choice and use of protecting groups and the reaction conditions to install and remove protecting groups are described in T. W. Green, *Protective Groups in Organic Synthesis* (Third Ed., Wiley, New York, 1999), which is incorporated herein by reference in its entirety.

Amino protecting groups are well known in the art and include those described in detail in T. W. Green, *Protective Groups in Organic Synthesis*. Amino protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl groups), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups; wherein each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups.

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups.

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N (R$^{ff}$)$_2$, —NR$^{ff}$C(=NR$^{ff}$)N(R$^{ff}$)$_2$, —NR$^{ff}$SO$_2$R$^{ee}$, —SO$_2$N (R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O) (R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S.

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R$^{ff}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{gg}$ groups; and each instance of R$^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$X, —NH(C$_{1-6}$ alkyl)$_2$X, —NH$_2$(C$_{1-6}$alkyl)X, —NH$_3$X, —N(OC$_{1-6}$ alkyl)(C$_{1-6}$ alkyl), —N(OH)(C$_{1-6}$ alkyl), —NH (OH), —SH, —SC$_{1-6}$ alkyl, —SS(C$_{1-6}$ alkyl), —C(=O) (C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N (C$_{1-6}$ alkyl)$_2$, —OC(=O)NH(C$_{1-6}$ alkyl), —NHC(=O) (C$_{1-6}$ alkyl), —N(C$_{1-6}$ alkyl)C(=O)(C$_{1-6}$ alkyl), —NHCO$_2$ (C$_{1-6}$alkyl), —NHC(=O)N(C$_{1-6}$ alkyl)$_2$, —NHC(=O)NH (C$_{1-6}$alkyl), —NHC(=O)NH$_2$, —C(=NH)O(C$_{1-6}$alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH) NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$alkyl), —SO$_2$N (C$_{1-6}$alkyl)$_2$, —SO$_2$NH(C$_{1-6}$alkyl), —SO$_2$NH$_2$, —SO$_2$C$_{1-6}$alkyl, —SO$_2$OC$_{1-6}$ alkyl, —OSO$_2$C$_{1-6}$alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S) SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal R$^{gg}$ substituents can be joined to form =O or =S;

wherein X$^-$ is a counterion.

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like) and carboxylate ions (e.g., acetate, ethanoate, propanoate, benzoate, glycerate, lactate, tartrate, glycolate, and the like).

For example, amino protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Amino protecting groups such as carbamate groups (e.g., —C(=O)OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Amino protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethyl silylethanesulfonamide (SES), 9-anthracenesulfonamide, 4-(4',8'-dimethoxynaphthylmethyl)benzenesulfonamide (DNMBS), benzylsulfonamide, trifluoromethyl sulfonamide, and phenacylsulfonamide.

Other amino protecting groups include, but are not limited to, phenothiazinyl-(10)-carbonyl derivative, N'-p-toluenesulfonylaminocarbonyl derivative, N'-phenylaminothiocarbonyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentacarbonylchromium- or tungsten)carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide and 3-nitropyridinesulfenamide (Npys).

As used herein, and unless otherwise indicated, acronyms or symbols for groups or reagents have the following definition: HPLC=high performance liquid chromatography; TFA=trifluoroacetic acid; TFE=2,2,2-trifluoroethanol, THF=tetrahydrofuran; CH$_3$CN=acetonitrile; HOAc=acetic acid; DCM=dichloromethane.

As used herein, and unless otherwise indicated, the term "substituted" or "substitution," when used to describe a chemical structure or moiety, refers to a derivative of that structure or moiety wherein one or more of its hydrogen atoms is replaced with a substituent such as, but not limited to: alkyl, alkenyl, alkynyl, and cycloalkyl; alkoxyalkyl; aroyl; halo; haloalkyl (e.g., trifluoromethyl); heterocycloalkyl; haloalkoxy (e.g., trifluoromethoxy); hydroxy; alkoxy; cycloalkyloxy; heterocylooxy; oxo; alkanoyl; aryl; heteroaryl (e.g., indolyl, imidazolyl, furyl, thienyl, thiazolyl, pyrrolidyl, pyridyl, and pyrimidyl); arylalkyl; alkylaryl; heteroaryl; heteroarylalkyl; alkylheteroaryl; heterocyclo; heterocycloalkyl-alkyl; aryloxy, alkanoyloxy; amino; alkylamino; arylamino; arylalkylamino; cycloalkylamino; heterocycloamino; mono- and di-substituted amino; alkanoylamino; aroylamino; aralkanoylamino; aminoalkyl; carbamyl (e.g., $CONH_2$); substituted carbamyl (e.g., $CONH$-alkyl, $CONH$-aryl, $CONH$-arylalkyl or instances where there are two substituents on the nitrogen); carbonyl; alkoxycarbonyl; carboxy; cyano; ester; ether; guanidino; nitro; sulfonyl; alkylsulfonyl; arylsulfonyl; arylalkylsulfonyl; sulfonamido (e.g., $SO_2NH_2$); substituted sulfonamido; thiol; alkylthio; arylthio; arylalkylthio; cycloalkylthio; heterocyclothio; alkylthiono; arylthiono; and arylalkylthiono. In some embodiments, a substituent itself may be substituted with one or more chemical moieties such as, but not limited to, those described herein.

As used herein, and unless otherwise indicated, the term "about" is used to specify that the values given are approximate. For example, the term "about," where it is used in connection with reaction temperatures, denotes that the temperature deviations within 30%, 25%, 20%, 15%, 10%, or 5% are encompassed by the temperature indicated. Similarly, the term "about," where it is used in connection with reaction time, denotes that the time period deviations within 30%, 25%, 20%, 15%, 10%, or 5% are encompassed by the time period indicated.

As used herein, and unless otherwise specified, a "suitable leaving group" refers to any atom or group of atoms that can leave the carbon atom to which it is attached. Specifically, a suitable leaving group is one that can be displaced by an approaching nucleophile. Those of ordinary skill in the art can determine what atom or group of atoms can serve as a suitable leaving group. In addition, routine experimentation can identify whether any specific atom or group of atoms can serve as a suitable leaving group. Preferred suitable leaving groups include those that are primary (e.g., a primary halo), although leaving groups that are secondary may also be used. Examples of suitable leaving groups include halogens and sulfonate esters. Among the halogens, bromo, chloro, iodo, and fluoro are preferred, with bromo and chloro being particularly preferred halogen-type leaving groups. With respect to sulfonate esters, methanesulfonate, trifluoromethanesulfonate, trichloromethanesulfonate, 2,2,2-trifluoroethanesulfonate, 2,2,2-trichloroethanesulfonate, and para-toluenesulfonate are particularly preferred, although other sulfonate esters and similarly constituted leaving groups known to those of ordinary skill in the art can be used as well.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

6.2 Processes 6.2.1 Preparation of Compound (I)

As depicted in Scheme 1 below, provided herein are processes for the preparation of an enantiomerically enriched or enantiomerically pure compound of Formula (I), or a pharmaceutically acceptable form thereof, comprising: (step 1.1) transforming an enantiomerically enriched or enantiomerically pure compound of Formula (II), or a salt thereof, to an enantiomerically enriched or enantiomerically pure compound of Formula (III), or a salt thereof; (step 1.2) cyclizing the enantiomerically enriched or enantiomerically pure compound of Formula (III) to an enantiomerically enriched or enantiomerically pure compound of Formula (I-a); (step 1.3) where Y is not hydrogen, deprotecting the enantiomerically enriched or enantiomerically pure compound of Formula (I-a) to an enantiomerically enriched or enantiomerically pure compound of Formula (I); and (step 1.4) optionally transforming the enantiomerically enriched or enantiomerically pure compound of Formula (I) to a pharmaceutically acceptable salt. In one embodiment, the formation of the glutarimide ring in the compound of Formula (I) occurs with high preservation of the configuration of the chiral center. In one embodiment, the process is efficient and scalable.

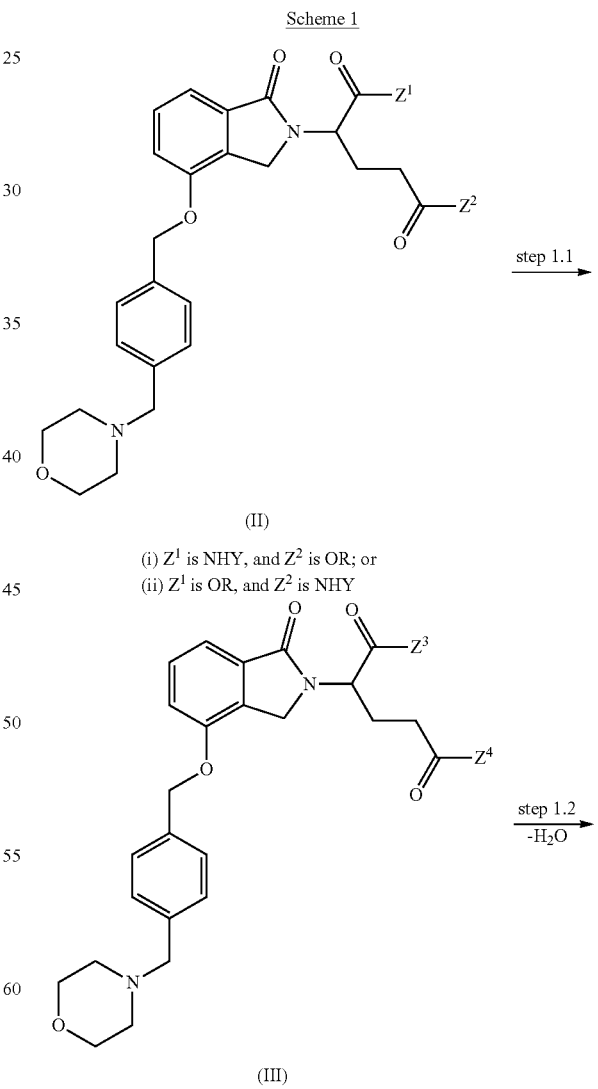

Scheme 1

(II)

(i) $Z^1$ is NHY, and $Z^2$ is OR; or
(ii) $Z^1$ is OR, and $Z^2$ is NHY step 1.1

(III)

(i) $Z^3$ is NHY, and $Z^4$ is OH; or
(ii) $Z^3$ is OH, and $Z^4$ is NHY step 1.2
$-H_2O$

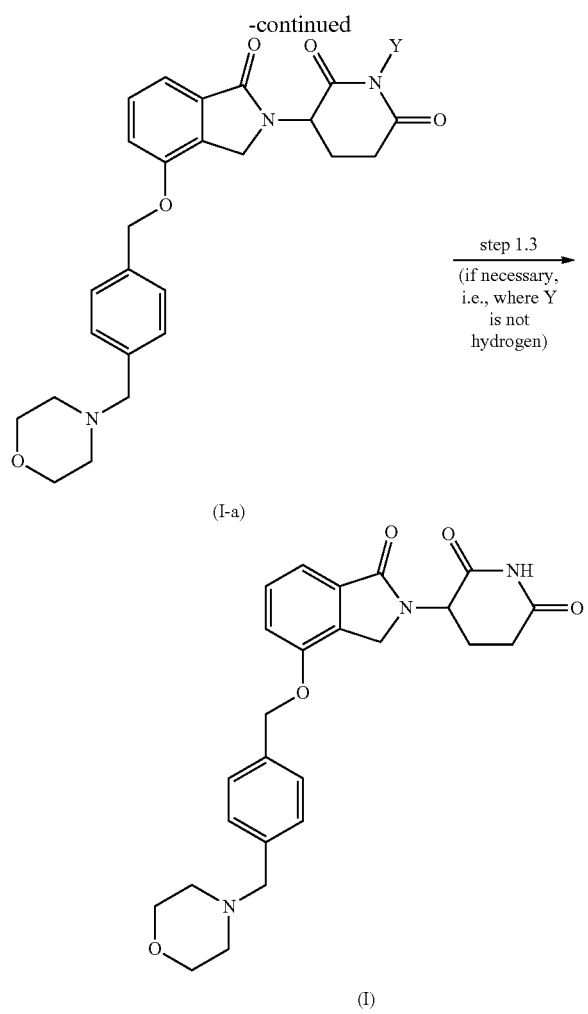

R may be a suitable carboxy protecting group, including methyl, tert-butyl, benzyl, and the like. Other suitable protecting groups are well known to those of ordinary skill in the art. Y may be any suitable amino protecting group. The choice and use of protecting groups and the reaction conditions to install and remove protecting groups are described in T. W. Green, *Protective Groups in Organic Synthesis* (Third Ed., Wiley, New York, 1999), which is incorporated herein by reference in its entirety.

In one embodiment, provided herein is a process for preparing an enantiomerically enriched or enantiomerically pure compound of Formula (I), or a pharmaceutically acceptable form thereof, comprising:

(step 1.1) transforming an enantiomerically enriched or enantiomerically pure compound of Formula (II), or a salt thereof, wherein
(i) $Z^1$ is NHY, and $Z^2$ is OR; or
(ii) $Z^1$ is OR, and $Z^2$ is NHY; wherein
R is substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted aralkyl, or a suitable protecting group of a carboxy group; and
Y is hydrogen, or a suitable amino protecting group;
to an enantiomerically enriched or enantiomerically pure compound of Formula (III), or a salt thereof, wherein
(i) $Z^3$ is NHY, and $Z^4$ is OH; or
(ii) $Z^3$ is OH, and $Z^4$ is NHY;
under conditions suitable for ester to acid transformation;
(step 1.2) cyclizing the enantiomerically enriched or enantiomerically pure compound of Formula (III) to an enantiomerically enriched or enantiomerically pure compound of Formula (I-a) under conditions suitable for cyclization;
(step 1.3) where Y is not hydrogen, deprotecting the enantiomerically enriched or enantiomerically pure compound of Formula (I-a) to an enantiomerically enriched or enantiomerically pure compound of Formula (I) under conditions suitable for deprotection; and
(step 1.4) optionally transforming the enantiomerically enriched or enantiomerically pure compound of Formula (I) to a pharmaceutically acceptable salt thereof under conditions suitable for salt formation.

In one embodiment, the compound of Formula (I) is (S)-3-(4-((4-(morpholinomethyl)benzyl)oxy)-1-oxoisoindolin-2-yl)piperidine-2,6-dione, which is also known as (3S)-3-(4-{[4-(morpholin-4-ylmethyl)benzyl]oxy}-1-oxo-1,3-dihydro-2H-isoindol-2-yl)piperidine-2,6-dione, or 2,6-piperidinedione, 3-[1,3-dihydro-4-[[4-(4-morpholinylmethyl)phenyl]methoxy]-1-oxo-2H-isoindol-2-yl]-, (3S)—.

In one embodiment, R is $C_{1-6}$ alkyl; $C_{3-6}$ cycloalkyl; $C_{1-6}$ haloalkyl; $C_{2-10}$ heteroalkyl; $C_{3-6}$ heterocycloalkyl; $C_{1-6}$ alkyl or $C_{2-10}$ heteroalkyl substituted with 1 to 3 aryl; or —$SiR^a_3$, wherein each $R^a$ is independently $C_{1-6}$ alkyl or $C_{5-14}$ aryl.

In one embodiment, R is methyl, ethyl, propyl, isopropyl, cyclopropyl, butyl, isobutyl, tert-butyl, methoxymethyl (MOM), methylthiomethyl (MTM), tetrahydropyranyl (THP), methoxyethoxymethyl (MEM), 2-(trimethylsilyl)ethoxymethylamine (SEM), benzyloxymethyl (BOM), 2-(trimethylsilyl)ethyl (TMSE), 2,2,2-trichloroethyl, benzyl, triphenylmethyl, p-methoxybenzyl, 2,6-dimethoxybenzyl, trimethylsilyl (TMS), triethylsilyl (TES), triisopropylsilyl (TIPS), dimethylisopropylsilyl (IPDMS), diethylisopropylsilyl (DEIPS), t-butyldimethylsilyl (TBDMS), or t-butyldiphenylsilyl (TBDPS). In one embodiment, R is methyl, tert-butyl, or benzyl. In one embodiment, R is methyl. In another embodiment, R is tert-butyl. In yet another embodiment, R is benzyl.

In one embodiment, Y is hydrogen.

In one embodiment, Y is a suitable amino protecting group. In one embodiment, Y is allyl, t-butyl, methoxymethyl (MOM), methylthiomethyl (MTM), benzyloxymethyl (BOM), 2,2,2-trichloroethoxymethyl, t-butyldimethylsiloxymethyl, pivaloyloxymethyl, cyanomethyl, pyrrolidinomethyl, methoxy, benzyloxy, methylthio, triphenylmethylthio, t-butyldimethylsilyl (TBDMS), triisopropylsilyl (TIPS), 4-methoxyphenyl, 4-(methyoxymethoxy)phenyl, 2-methoxy-1-naphthyl, benzyl, 4-methoxybenzyl, 2,4-dimethoxybenzyl, 3,4-dimethoxybenzyl, 2-acetoxy-4-methoxybenzyl, 2-nitrobenzyl, bis(4-methoxyphenyl)methyl (DAM), bis(4-methoxyphenyl)phenylmethyl, bis(4-methylsulfinylphenyl)methyl, triphenylmethyl (Tr), 9-phenylfluorenyl (Pf), bis(trimethylsilyl)methyl, t-butoxycarbonyl (BOC), benzyloxycarbonyl (Cbz), methoxycarbonyl, ethoxycarbonyl, p-toluenesulfonyl (Ts), butenyl, (E)-2-(methoxycarbonyl)vinyl, diethoxymethyl, 1-methoxy-2,2-dimethylpropyl, or 2-(4-methylphenylsulfonyl)ethyl. In one embodiment, Y is benzyl, 4-methoxybenzyl, t-butyldimethylsilyl, t-butoxycarbonyl, or benzyloxycarbonyl. In one embodiment, Y is benzyl.

Methods for transforming an ester to an acid (step 1.1) are well known to those of ordinary skill in the art. See generally, T. W. Green, *Protective Groups in Organic Synthesis* (Third Ed., Wiley, New York, 1999).

In one embodiment, step 1.1 occurs in the presence of an acid. In some embodiments, the acid is generated in situ. In one embodiment, step 1.1 occurs in the presence of an organic acid. In one embodiment, step 1.1 occurs in the presence of $R^b$COOH wherein $R^b$ is hydrogen, substituted or unsubstituted $C_{1-10}$ alkyl, substituted or unsubstituted $C_{1-10}$ haloalkyl, or substituted or unsubstituted $C_{5-14}$ aryl. In one embodiment, step 1.1 occurs in the presence of formic acid, acetic acid, trifluoroacetic acid, or benzoic acid.

In one embodiment, step 1.1 occurs in the presence of $R^b$SO$_3$H wherein $R^b$ is hydrogen, substituted or unsubstituted $C_{1-10}$ alkyl, substituted or unsubstituted $C_{1-10}$ haloalkyl, or substituted or unsubstituted $C_{5-14}$ aryl. In one embodiment, step 1.1 occurs in the presence of sulfonic acid, benzenesulfonic acid, p-toluenesulfonic acid, camphorsulfonic acid, methanesulfonic acid, or trifluoromethanesulfonic acid. In one embodiment, step 1.1 occurs in the presence of benzenesulfonic acid, p-toluenesulfonic acid, camphorsulfonic acid, or methanesulfonic acid. In one embodiment, step 1.1 occurs in the presence of benzenesulfonic acid. In another embodiment, step 1.1 occurs in the presence of p-toluenesulfonic acid. In yet another embodiment, step 1.1 occurs in the presence of camphorsulfonic acid. In yet another embodiment, step 1.1 occurs in the presence of methanesulfonic acid.

In one embodiment, step 1.1 occurs in the presence of an inorganic acid. In one embodiment, step 1.1 occurs in the presence of hydrochloric acid, sulfuric acid, nitric acid, or phosphoric acid. In one embodiment, step 1.1 occurs in the presence of hydrochloric acid.

In one embodiment, step 1.1 occurs in the presence of a base. In some embodiments, the base is generated in situ. In one embodiment, step 1.1 occurs in the presence of an alkali metal base. In one embodiment, step 1.1 occurs in the presence of an alkali metal hydroxide, carbonate, hydrogencarbonate, phosphate, hydrogenphosphate, or dihydrogenphosphate. In one embodiment, step 1.1 occurs in the presence of LiOH, NaOH, KOH, Na$_2$CO$_3$, K$_2$CO$_3$, Cs$_2$CO$_3$, NaHCO$_3$, KHCO$_3$, Na$_3$PO$_4$, K$_3$PO$_4$, Na$_2$HPO$_4$, K$_2$HPO$_4$, NaH$_2$PO$_4$, or KH$_2$PO$_4$.

In one embodiment, step 1.1 occurs in the presence of M-$R^c$ or M-O$R^c$, wherein M is alkali metal; and $R^c$ is substituted or unsubstituted $C_{1-10}$ alkyl. In one embodiment, step 1.1 occurs in the presence of sodium methoxide, sodium ethoxide, sodium t-butoxide, potassium methoxide, potassium ethoxide, or potassium t-butoxide. In one embodiment, step 1.1 occurs in the presence of sodium t-butoxide, or potassium t-butoxide.

In one embodiment, step 1.1 occurs in the presence of a nitrogen containing base. In one embodiment, step 1.1 occurs in the presence of NH$_4$OH, triethylamine, diisopropylethylamine, pyridine, 4-dimethylaminopyridine, imidazole, or 1,8-diazabicyclo[5.4.0]undec-7-ene (DBU).

In one embodiment, step 1.1 occurs by hydrogenation.

The cyclization of a compound of Formula (III) (step 1.2) may occur with any dehydrating agent or any combination of dehydrating agents according to a person of ordinary skill in the art. In some embodiments, the dehydrating agent is (or the combination of dehydrating agents are) generated in situ. In some embodiments, the dehydrating agent is (or the combination of dehydrating agents contains) thionyl chloride, sulfuryl chloride, 4-dimethylaminopyridine, phosgene, diphosgene, triphosgene, oxalyl chloride, a carbodiimide, an anhydride or a mixed anhydride, a phenol, or a compound of Formula (A):

wherein each of $A^1$ and $A^2$ is independently an unsubstituted or substituted heteroaryl group. In some embodiments, the dehydrating agent is (or combination of dehydrating agents contains) benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4(3H)-one (DEPBT), 1-ethyl-3-(3-dimethyllaminopropyl)carbodiimide (EDCI), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU), O-(3,4-dihydro-4-oxo-1,2,3-benzotriazine-3-yl)-N,N,N,N-tetramethyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt). In some embodiments, the dehydrating agent is 1-ethyl-3-(3-dimethyllaminopropyl)carbodiimide (EDCI) or 2-(1H-benzotriazole-1-yl)-1,1,3,3-tetramethyluronium tetrafluoroborate (TBTU). In another embodiment, the dehydrating agent is molecular sieve.

The cyclization of a compound of Formula (III) (step 1.2) may occur when water is removed from the reaction mixture. In one embodiment of step 1.2, water is removed by azeotropic distillation. Other techniques to remove water from a reaction mixture are well known to those of ordinary skill in the art.

The cyclization of a compound of Formula (III) (step 1.2) may also occur in the absence of dehydrating agent or without removal of water.

In one embodiment, wherein Y is hydrogen, a compound of Formula (I-a) is a compound of Formula (I), and step 1.3 is not necessary.

In one embodiment, wherein Y is not a hydrogen, a compound of Formula (I-a) is not a compound of Formula (I), and step 1.3 is necessary. The reaction conditions to install and remove suitable amino protecting groups are well known to those of ordinary skill in the art, including those described in T. W. Green, *Protective Groups in Organic Synthesis* (Third Ed., Wiley, New York, 1999). In one embodiments, Y is benzyl, and step 1.3 occurs by hydrogenation.

Optionally, the compound of Formula (I), or a salt thereof, may be transformed to a different pharmaceutically acceptable salt by reacting with an acid (step 1.4). In one embodiment, step 1.4 comprises transforming a free base of a compound of Formula (I) to a pharmaceutically acceptable salt thereof. In another embodiment, step 1.4 comprises transforming a salt of a compound of Formula (I) to a free base, and transforming the free base to a pharmaceutically acceptable salt thereof. In yet another embodiments, step 1.4 comprises directly transforming a salt of a compound of Formula (I) to a different pharmaceutically acceptable salt thereof. In one embodiment, the pharmaceutically acceptable salt is hydrochloride.

In one embodiment, as depicted in Scheme 1a below, step 1.1 and step 1.2 occur in one-pot, without isolation of the compound of Formula (III).

Scheme 1a

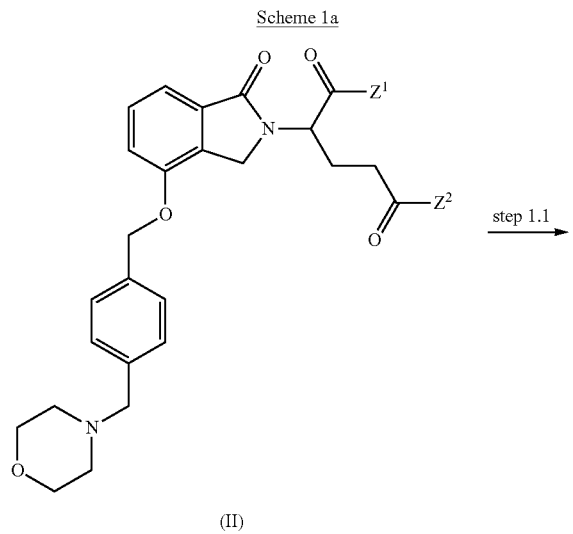

(II)

(i) $Z^1$ is NHY, and $Z^2$ is OR; or
(ii) $Z^1$ is OR, and $Z^2$ is NHY

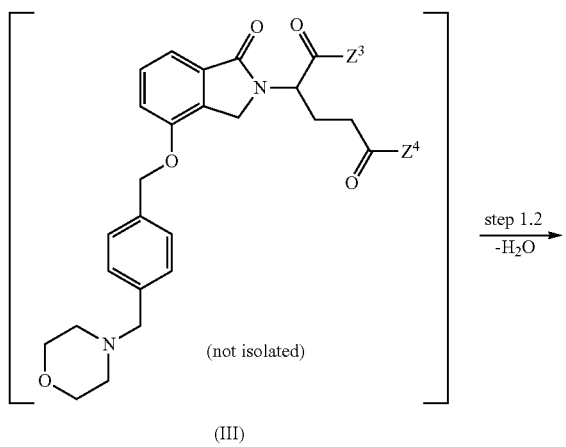

(III)

(i) $Z^3$ is NHY, and $Z^4$ is OH; or
(ii) $Z^3$ is OH, and $Z^4$ is NHY

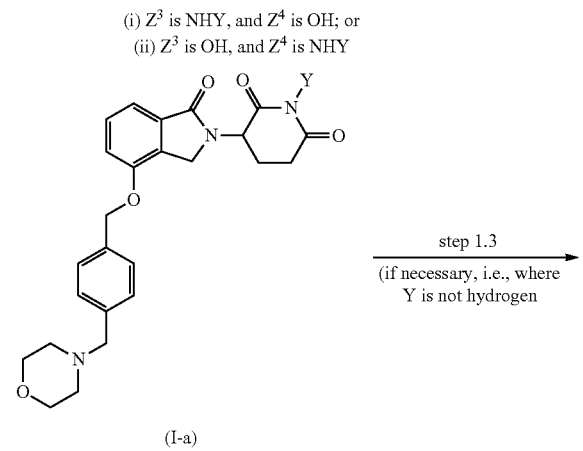

(I-a)

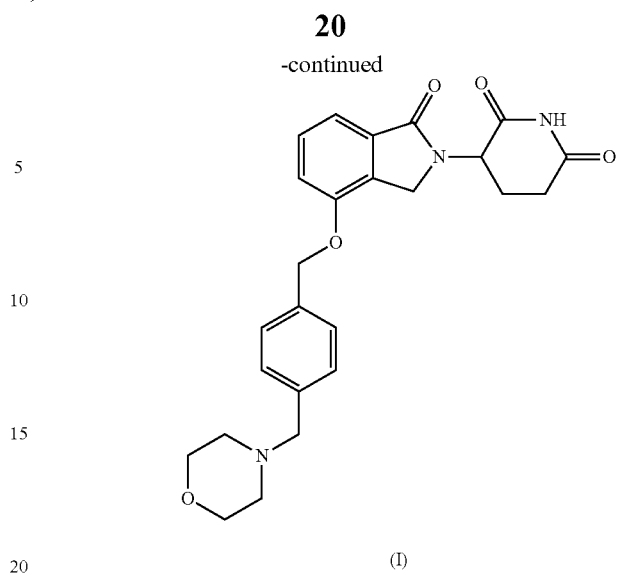

(I)

In one embodiment, provided herein is a process for preparing an enantiomerically enriched or enantiomerically pure compound of Formula (I), or a pharmaceutically acceptable form thereof, comprising: (step 1.1) transforming an enantiomerically enriched or enantiomerically pure compound of Formula (II), or a salt thereof, wherein
(i) $Z^1$ is NHY, and $Z^2$ is OR; or
(ii) $Z^1$ is OR, and $Z^2$ is NHY; wherein
R is substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted aralkyl, or a suitable protecting group of a carboxy group; and
Y is hydrogen, or a suitable amino protecting group;
to an enantiomerically enriched or enantiomerically pure compound of Formula (III), or a salt thereof, wherein
(i) $Z^3$ is NHY, and $Z^4$ is OH; or
(ii) $Z^3$ is OH, and $Z^4$ is NHY;
under conditions suitable for ester to acid transformation;
(step 1.2) cyclizing the enantiomerically enriched or enantiomerically pure compound of Formula (III) to an enantiomerically enriched or enantiomerically pure compound of Formula (I-a) under conditions suitable for cyclization;
(step 1.3) where Y is not hydrogen, deprotecting the enantiomerically enriched or enantiomerically pure compound of Formula (I-a) to an enantiomerically enriched or enantiomerically pure compound of Formula (I) under conditions suitable for deprotection; and
(step 1.4) optionally transforming the enantiomerically enriched or enantiomerically pure compound of Formula (I) to a pharmaceutically acceptable salt thereof under conditions suitable for salt formation;
wherein step 1.1 and step 1.2 occur in one-pot.

In one embodiment, the compound of Formula (I) is (S)-3-(4-((4-(morpholinomethyl)benzyl)oxy)-1-oxoisoindolin-2-yl)piperidine-2,6-dione.

In one embodiment, step 1.1 and step 1.2 occur in one-pot; and R is $C_{1-6}$ alkyl; $C_{3-6}$ cycloalkyl; $C_{1-6}$ haloalkyl; $C_{2-10}$ heteroalkyl; $C_{3-6}$ heterocycloalkyl; $C_{1-6}$ alkyl or $C_{2-10}$ heteroalkyl substituted with 1 to 3 aryl; or —$SiR^a{}_3$ wherein each $R^a$ is independently $C_{1-6}$ alkyl or $C_{5-14}$ aryl.

In one embodiment, step 1.1 and step 1.2 occur in one-pot; and R is methyl, ethyl, propyl, isopropyl, cyclopropyl, butyl, isobutyl, tert-butyl, methoxymethyl (MOM), methylthiomethyl (MTM), tetrahydropyranyl (THP), methoxyethoxymethyl (MEM), 2-(trimethyl silyl)ethoxymethylamine (SEM), benzyloxymethyl (BOM), 2-(trimethylsilyl)ethyl (TMSE), 2,2,2-trichloroethyl, benzyl, triphenylmethyl, p-methoxybenzyl, 2,6-dimethoxybenzyl, trimethylsilyl (TMS), triethylsilyl (TES), triisopropylsilyl (TIPS), dimethylisopropylsilyl (IPDMS), diethylisopropylsilyl (DEIPS), t-butyldimethylsilyl (TBDMS), or t-butyldiphenylsilyl (TBDPS). In one embodiment, step 1.1 and step 1.2 occur in one-pot; and R is methyl, tert-butyl, or benzyl. In one embodiment, step 1.1 and step 1.2 occur in one-pot; and R is methyl. In another embodiment, step 1.1 and step 1.2 occur in one-pot; and R is tert-butyl. In yet another embodiment, step 1.1 and step 1.2 occur in one-pot; and R is benzyl.

In one embodiment, step 1.1 and step 1.2 occur in one-pot; and Y is hydrogen.

In one embodiment, step 1.1 and step 1.2 occur in one-pot; and Y is a suitable amino protecting group. In one embodiment, step 1.1 and step 1.2 occur in one-pot; and Y is allyl, t-butyl, methoxymethyl (MOM), methylthiomethyl (MTM), benzyloxymethyl (BOM), 2,2,2-trichloroethoxymethyl, t-butyldimethylsiloxymethyl, pivaloyloxymethyl, cyanomethyl, pyrrolidinomethyl, methoxy, benzyloxy, methylthio, triphenylmethylthio, t-butyldimethylsilyl (TBDMS), triisopropylsilyl (TIPS), 4-methoxyphenyl, 4-(methyoxymethoxy)phenyl, 2-methoxy-1-naphthyl, benzyl, 4-methoxybenzyl, 2,4-dimethoxybenzyl, 3,4-dimethoxybenzyl, 2-acetoxy-4-methoxybenzyl, 2-nitrobenzyl, bis(4-methoxyphenyl)methyl (DAM), bis(4-methoxyphenyl)phenylmethyl, bis(4-methylsulfinylphenyl)methyl, triphenylmethyl (Tr), 9-phenylfluorenyl (Pf), bis(trimethylsilyl)methyl, t-butoxycarbonyl (BOC), benzyloxycarbonyl (Cbz), methoxycarbonyl, ethoxycarbonyl, p-toluenesulfonyl (Ts), butenyl, (E)-2-(methoxycarbonyl)vinyl, diethoxymethyl, 1-methoxy-2,2-dimethylpropyl, or 2-(4-methylphenylsulfonyl)ethyl. In one embodiment, step 1.1 and step 1.2 occur in one-pot; and Y is benzyl, 4-methoxybenzyl, t-butyldimethylsilyl, t-butoxycarbonyl, or benzyloxycarbonyl. In one embodiment, step 1.1 and step 1.2 occur in one-pot; and Y is benzyl.

In one embodiment, step 1.1 and step 1.2 occur in one-pot by hydrogenation. In one embodiment, R is benzyl, and step 1.1 and step 1.2 occur in one-pot by hydrogenation.

In one embodiment, step 1.1 and step 1.2 occur in one-pot by hydrogenation/cyclization, wherein the cyclization is promoted by an acid or base.

In one embodiment, step 1.1 and step 1.2 occur in one-pot in the presence of a base. In one embodiment, step 1.1 and step 1.2 occur in one-pot in the presence of an alkali metal hydroxide, carbonate, hydrogencarbonate, phosphate, hydrogenphosphate, or dihydrogenphosphate. In one embodiment, step 1.1 and step 1.2 occur in one-pot in the presence of LiOH, NaOH, KOH, $Na_2CO_3$, $K_2CO_3$, $Cs_2CO_3$, $NaHCO_3$, $KHCO_3$, $Na_3PO_4$, $K_3PO_4$, $Na_2HPO_4$, $K_2HPO_4$, $NaH_2PO_4$, or $KH_2PO_4$. In one embodiment, R is methyl, and step 1.1 and step 1.2 occur in one-pot in the presence of NaOH or KOH.

In one embodiment, step 1.1 and step 1.2 occur in one-pot in the presence of M-$R^c$ or M-$OR^c$, wherein M is alkali metal; and $R^c$ is substituted or unsubstituted $C_{1-10}$ alkyl. In one embodiment, step 1.1 and step 1.2 occur in one-pot in the presence of sodium methoxide, sodium ethoxide, sodium t-butoxide, potassium methoxide, potassium ethoxide, or potassium t-butoxide. In one embodiment, R is methyl, and step 1.1 and step 1.2 occur in one-pot in the presence of sodium tert-butoxide, or potassium tert-butoxide.

In one embodiment, step 1.1 and step 1.2 occur in one-pot in the presence of an acid. In some embodiments, the acid is generated in situ. In one embodiment, step 1.1 and step 1.2 occur in one-pot in the presence of an organic acid. In one embodiment, step 1.1 and step 1.2 occur in one-pot in the presence of $R^b$COOH wherein $R^b$ is hydrogen, substituted or unsubstituted $C_{1-10}$ alkyl, substituted or unsubstituted $C_{1-10}$ haloalkyl, or substituted or unsubstituted $C_{5-14}$ aryl. In one embodiment, step 1.1 and step 1.2 occur in one-pot in the presence of formic acid, acetic acid, trifluoroacetic acid, or benzoic acid. In one embodiment, R is tert-butyl, and step 1.1 and step 1.2 occur in one-pot in the presence of trifluoroacetic acid.

In one embodiment, step 1.1 and step 1.2 occur in one-pot in the presence of a Brønsted or Lewis acid. In some embodiments, the acid is generated in situ.

In one embodiment, step 1.1 and step 1.2 occur in one-pot in the presence of $R^bSO_3H$ wherein $R^b$ is hydrogen, substituted or unsubstituted $C_{1-10}$ alkyl, substituted or unsubstituted $C_{1-10}$ haloalkyl, or substituted or unsubstituted $C_{5-14}$ aryl. In one embodiment, step 1.1 and step 1.2 occur in one-pot in the presence of sulfonic acid, benzenesulfonic acid, p-toluenesulfonic acid, camphorsulfonic acid, methanesulfonic acid, or trifluoromethanesulfonic acid. In one embodiment, step 1.1 and step 1.2 occur in one-pot in the presence of benzenesulfonic acid, p-toluenesulfonic acid, camphorsulfonic acid, or methanesulfonic acid. In one embodiment, step 1.1 and step 1.2 occur in one-pot in the presence of benzenesulfonic acid. In another embodiment, step 1.1 and step 1.2 occur in one-pot in the presence of p-toluenesulfonic acid. In yet another embodiment, step 1.1 and step 1.2 occur in one-pot in the presence of camphorsulfonic acid. In yet another embodiment, step 1.1 and step 1.2 occur in one-pot in the presence of methanesulfonic acid. In one embodiment, R is tert-butyl, and step 1.1 and step 1.2 occur in one-pot in the presence of benzenesulfonic acid.

In one embodiment, step 1.1 and step 1.2 occur in one-pot in the presence of an inorganic acid. In one embodiment, step 1.1 and step 1.2 occur in one-pot in the presence of hydrochloric acid, sulfuric acid, nitric acid, or phosphoric acid. In one embodiment, step 1.1 and step 1.2 occur in one-pot in the presence of hydrochloric acid. In one embodiment, R is tert-butyl, and step 1.1 and step 1.2 occur in one-pot in the presence of hydrochloric acid.

Step 1.1 and step 1.2, separately or in one-pot, may occur in any solvent or any combination of solvents. In some embodiments, the solvent is, or the combination of solvents contains, diethyl ether, 1,4-dioxane, tetrahydrofuran, ethyl acetate, isopropyl acetate, acetonitrile, methanol, ethanol, isopropyl alcohol, dimethylformamide, dimethyl sulfoxide, glyme, diglyme, dimethylacetamide, or N-methyl-2-pyrrolidone. In some embodiments, the solvent is acetonitrile.

Step 1.1 and step 1.2, separately or in one-pot, may occur at any reaction temperature. In some embodiments, the reaction temperature is from about −100° C. to about 200° C. In some embodiments, the reaction temperature is from about −50° C. to about 150° C. In some embodiments, the reaction temperature is from about 0° C. to about 100° C. In some embodiments, the reaction temperature is from about 85° C. to about 95° C. In some embodiments, the reaction temperature is about 90° C.

Step 1.1 and step 1.2, separately or in one-pot, may occur at any reaction time. In some embodiments, the reaction time is from about 1 minute to about 14 days. In some embodiments, the reaction time is from about 5 minute to about 48 hours. In some embodiments, the reaction time is from about 1 hour to about 24 hours. In some embodiments, the reaction time is from about 3 hours to about 12 hours. In some embodiments, the reaction time is from about 8 hours to about 9 hours.

In one exemplary embodiment, Y is hydrogen, R is tert-butyl, and step 1.1 and step 1.2 occur in one-pot in the presence of benzenesulfonic acid, wherein the solvent is acetonitrile, the reaction temperature is about 90° C., and the reaction time is from about 8 hours to about 9 hours.

In one exemplary embodiment, Y is hydrogen, R is tert-butyl, and step 1.1 and step 1.2 occur in one-pot in the presence of benzenesulfonic acid, wherein the solvent is acetonitrile, the reaction temperature is about 90° C., the reaction time is from about 8 hours to about 9 hours, and water is removed by azeotropic distillation.

Steps 1.3 and 1.4 are as described above and herein.

In another embodiment, as depicted in Scheme 1b below, without being limited to any intermediate or any theory, a compound of Formula (I-a) can be prepared from a compound of Formula (II) in one step.

Scheme 1b

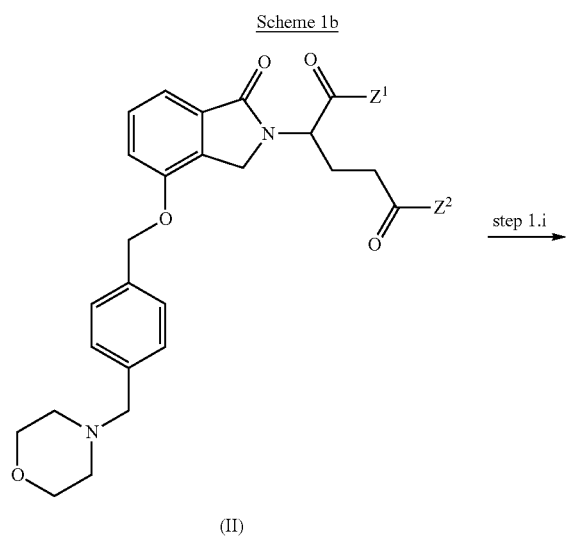

(II)

(i) $Z^1$ is NHY, and $Z^2$ is OR; or
(ii) $Z^1$ is OR, and $Z^2$ is NHY

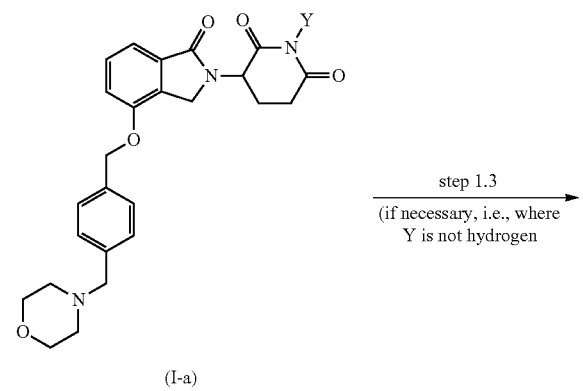

step 1.3
(if necessary, i.e., where Y is not hydrogen)

(I-a)

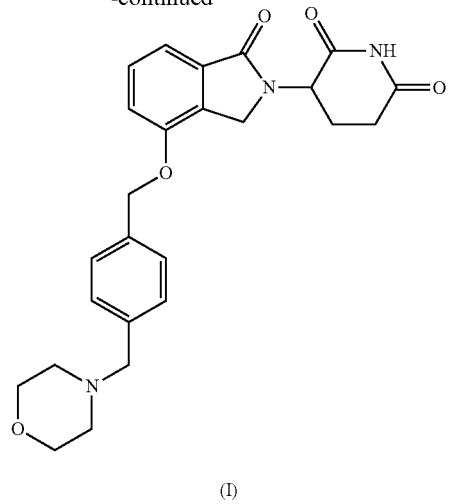

(I)

In one embodiment, provided herein is a process for preparing an enantiomerically enriched or enantiomerically pure compound of Formula (I), or a pharmaceutically acceptable form thereof, comprising:

(step 1.i) transforming an enantiomerically enriched or enantiomerically pure compound of Formula (II), or a salt thereof, wherein
(i) $Z^1$ is NHY, and $Z^2$ is OR; or
(ii) $Z^1$ is OR, and $Z^2$ is NHY; wherein
R is substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted aralkyl, or a suitable protecting group of a carboxy group; and
Y is hydrogen, or a suitable amino protecting group;
to an enantiomerically enriched or enantiomerically pure compound of Formula (I-a), or a salt thereof, under conditions suitable for cyclization;

(step 1.3) where Y is not hydrogen, deprotecting the enantiomerically enriched or enantiomerically pure compound of Formula (I-a) to an enantiomerically enriched or enantiomerically pure compound of Formula (I) under conditions suitable for deprotection; and (step 1.4) optionally transforming the enantiomerically enriched or enantiomerically pure compound of Formula (I) to a pharmaceutically acceptable salt thereof under conditions suitable for salt formation.

In one embodiment, the compound of Formula (I) is (S)-3-(4-((4-(morpholinomethyl)benzyl)oxy)-1-oxoisoindolin-2-yl)piperidine-2,6-dione.

In one embodiment, R is $C_{1-6}$ alkyl; $C_{3-6}$ cycloalkyl; $C_{1-6}$ haloalkyl; $C_{2-10}$ heteroalkyl; $C_{3-6}$ heterocycloalkyl; $C_{1-6}$ alkyl or $C_{2-10}$ heteroalkyl substituted with 1 to 3 aryl; or —SiR$^a_3$, wherein each R$^a$ is independently $C_{1-6}$ alkyl or $C_{5-14}$ aryl.

In one embodiment, R is methyl, ethyl, propyl, isopropyl, cyclopropyl, butyl, isobutyl, tert-butyl, methoxymethyl (MOM), methylthiomethyl (MTM), tetrahydropyranyl (THP), methoxyethoxymethyl (MEM), 2-(trimethylsilyl)ethoxymethylamine (SEM), benzyloxymethyl (BOM), 2-(trimethylsilyl)ethyl (TMSE), 2,2,2-trichloroethyl, benzyl, triphenylmethyl, p-methoxybenzyl, 2,6-dimethoxybenzyl, trimethylsilyl (TMS), triethylsilyl (TES), triisopropylsilyl (TIPS), dimethylisopropylsilyl (IPDMS), diethylisopropylsilyl (DEIPS), t-butyldimethylsilyl (TB-DMS), or t-butyldiphenylsilyl (TBDPS). In one embodiment, R is methyl, tert-butyl, or benzyl. In one embodiment, R is methyl. In another embodiment, R is tert-butyl. In yet another embodiment, R is benzyl.

In one embodiment, Y is hydrogen.

In one embodiment, Y is a suitable amino protecting group. In one embodiment, Y is allyl, t-butyl, methoxymethyl (MOM), methylthiomethyl (MTM), benzyloxymethyl (BOM), 2,2,2-trichloroethoxymethyl, t-butyldimethylsiloxymethyl, pivaloyloxymethyl, cyanomethyl, pyrrolidinomethyl, methoxy, benzyloxy, methylthio, triphenylmethylthio, t-butyldimethylsilyl (TBDMS), triisopropylsilyl (TIPS), 4-methoxyphenyl, 4-(methyoxymethoxy)phenyl, 2-methoxy-1-naphthyl, benzyl, 4-methoxybenzyl, 2,4-dimethoxybenzyl, 3,4-dimethoxybenzyl, 2-acetoxy-4-methoxybenzyl, 2-nitrobenzyl, bis(4-methoxyphenyl)methyl (DAM), bis(4-methoxyphenyl)phenylmethyl, bis(4-methylsulfinylphenyl)methyl, triphenylmethyl (Tr), 9-phenylfluorenyl (Pf), bis(trimethylsilyl)methyl, t-butoxycarbonyl (BOC), benzyloxycarbonyl (Cbz), methoxycarbonyl, ethoxycarbonyl, p-toluenesulfonyl (Ts), butenyl, (E)-2-(methoxycarbonyl)vinyl, diethoxymethyl, 1-methoxy-2,2-dimethylpropyl, or 2-(4-methylphenylsulfonyl)ethyl. In one embodiment, Y is benzyl, 4-methoxybenzyl, t-butyldimethylsilyl, t-butoxycarbonyl, or benzyloxycarbonyl. In one embodiment, Y is benzyl.

In one embodiment, step 1.i occurs by hydrogenation. In one embodiment, R is benzyl, and step 1.i occurs by hydrogenation.

In one embodiment, step 1.i occurs in the presence of a base. In one embodiment, step 1.i occurs in the presence of an alkali metal hydroxide, carbonate, hydrogencarbonate, phosphate, hydrogenphosphate, or dihydrogenphosphate. In one embodiment, step 1.i occurs in the presence of LiOH, NaOH, KOH, $Na_2CO_3$, $K_2CO_3$, $Cs_2CO_3$, $NaHCO_3$, $KHCO_3$, $Na_3PO_4$, $K_3PO_4$, $Na_2HPO_4$, $K_2HPO_4$, $NaH_2PO_4$, or $KH_2PO_4$. In one embodiment, R is methyl, and step 1.i occurs in the presence of NaOH or KOH.

In one embodiment, step 1.i occurs in the presence of M-$R^c$ or M-$OR^c$, wherein M is alkali metal; and $R^c$ is substituted or unsubstituted $C_{1-10}$ alkyl. In one embodiment, step 1.i occurs in the presence of sodium methoxide, sodium ethoxide, sodium t-butoxide, potassium methoxide, potassium ethoxide, or potassium t-butoxide. In one embodiment, R is methyl, and step 1.i occurs in the presence of sodium tert-butoxide, or potassium tert-butoxide.

In one embodiment, step 1.i occurs in the presence of an acid. In some embodiments, the acid is generated in situ. In one embodiment, step 1.i occurs in the presence of an organic acid. In one embodiment, step 1.i occurs in the presence of $R^b$COOH wherein $R^b$ is hydrogen, substituted or unsubstituted $C_{1-10}$ alkyl, substituted or unsubstituted $C_{1-10}$ haloalkyl, or substituted or unsubstituted $C_{5-14}$ aryl. In one embodiment, step 1.i occurs in the presence of formic acid, acetic acid, trifluoroacetic acid, or benzoic acid. In one embodiment, R is tert-butyl, and step 1.i occurs in the presence of trifluoroacetic acid.

In one embodiment, step 1.i occurs in the presence of a Brønsted or Lewis acid. In some embodiments, the acid is generated in situ.

In one embodiment, step 1.i occurs in the presence of $R^bSO_3H$ wherein $R^b$ is hydrogen, substituted or unsubstituted $C_{1-10}$ alkyl, substituted or unsubstituted $C_{1-10}$ haloalkyl, or substituted or unsubstituted $C_{5-14}$ aryl. In one embodiment, step 1.i occurs in the presence of sulfonic acid, benzenesulfonic acid, p-toluenesulfonic acid, camphorsulfonic acid, methanesulfonic acid, or trifluoromethanesulfonic acid. In one embodiment, step 1.i occurs in the presence of benzenesulfonic acid, p-toluenesulfonic acid, camphorsulfonic acid, or methanesulfonic acid. In one embodiment, step 1.i occurs in the presence of benzenesulfonic acid. In another embodiment, step 1.i occurs in the presence of p-toluenesulfonic acid. In yet another embodiment, step 1.i occurs in the presence of camphorsulfonic acid. In yet another embodiment, step 1.i occurs in the presence of methanesulfonic acid. In one embodiment, R is tert-butyl, and step 1.i occurs in the presence of benzenesulfonic acid.

In one embodiment, step 1.i occurs in the presence of an inorganic acid. In one embodiment, step 1.i occurs in the presence of hydrochloric acid, sulfuric acid, nitric acid, or phosphoric acid. In one embodiment, step 1.i occurs in the presence of hydrochloric acid. In one embodiment, R is tert-butyl, and step 1.i occurs in the presence of hydrochloric acid.

Step 1.i may occur in any solvent or any combination of solvents. In some embodiments, the solvent is, or the combination of solvents contains, diethyl ether, 1,4-dioxane, tetrahydrofuran, ethyl acetate, isopropyl acetate, acetonitrile, methanol, ethanol, isopropyl alcohol, dimethylformamide, dimethyl sulfoxide, glyme, diglyme, dimethylacetamide, or N-methyl-2-pyrrolidone. In some embodiments, the solvent is acetonitrile.

Step 1.i may occur at any reaction temperature. In some embodiments, the reaction temperature is from about −100° C. to about 200° C. In some embodiments, the reaction temperature is from about −50° C. to about 150° C. In some embodiments, the reaction temperature is from about 0° C. to about 100° C. In some embodiments, the reaction temperature is from about 85° C. to about 95° C. In some embodiments, the reaction temperature is about 90° C.

Step 1.i may occur at any reaction time. In some embodiments, the reaction time is from about 1 minute to about 14 days. In some embodiments, the reaction time is from about 5 minute to about 48 hours. In some embodiments, the reaction time is from about 1 hour to about 24 hours. In some embodiments, the reaction time is from about 3 hours to about 12 hours. In some embodiments, the reaction time is from about 8 hours to about 9 hours.

In one exemplary embodiment, Y is hydrogen, R is tert-butyl, and step 1.i occurs in the presence of benzenesulfonic acid, wherein the solvent is acetonitrile, the reaction temperature is about 90° C., and the reaction time is from about 8 hours to about 9 hours.

In one exemplary embodiment, Y is hydrogen, R is tert-butyl, and step 1.i occurs in the presence of benzenesulfonic acid, wherein the solvent is acetonitrile, the reaction temperature is about 90° C., the reaction time is from about 8 hours to about 9 hours, and water is removed by azeotropic distillation.

In one exemplary embodiment, Y is benzyl, R is methyl, and step 1.i occurs in the presence of p-toluenesulfonic acid. In one exemplary embodiment, Y is benzyl, R is methyl, and step 1.i occurs in the presence of p-toluenesulfonic acid, wherein the solvent is acetic acid, the reaction temperature is about 100° C., the reaction time is about 8 hours.

Steps 1.3 and 1.4 are as described above and herein.

In another embodiment, deprotection of Y may occur concurrently with formation of the glutarimide ring. As depicted in Scheme 1c below, without being limited to any intermediate or any theory, a compound of Formula (I) can be prepared from a compound of Formula (II) in one step.

Scheme 1c

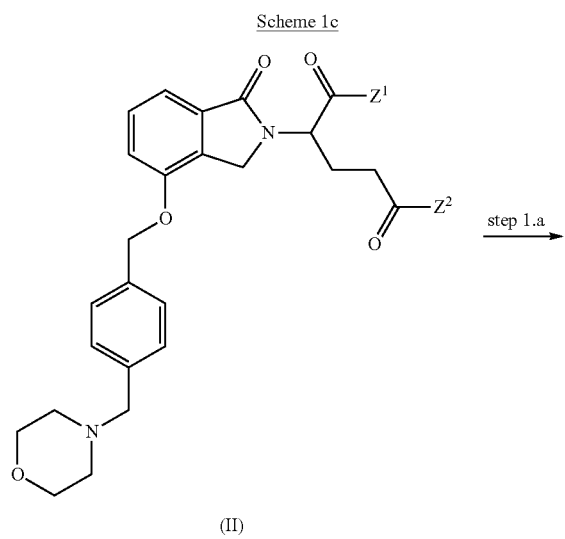

(i) $Z^1$ is NHY, and $Z^2$ is OR; or
(ii) $Z^1$ is OR, and $Z^2$ is NHY

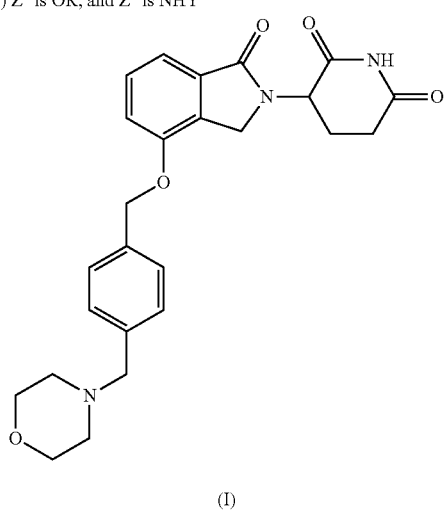

In one embodiment, provided herein is a process for preparing an enantiomerically enriched or enantiomerically pure compound of Formula (I), or a pharmaceutically acceptable form thereof, comprising:
(step 1.a) transforming an enantiomerically enriched or enantiomerically pure compound of Formula (II), or a salt thereof, wherein
(i) $Z^1$ is NHY, and $Z^2$ is OR; or
(ii) $Z^1$ is OR, and $Z^2$ is NHY; wherein
R is substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, substituted or unsubstituted aralkyl, or a suitable protecting group of a carboxy group; and
Y is hydrogen, or a suitable amino protecting group;
to an enantiomerically enriched or enantiomerically pure compound of Formula (I), or a salt thereof, under conditions suitable for cyclization and deprotection;
(step 1.4) optionally transforming the enantiomerically enriched or enantiomerically pure compound of Formula (I) to a pharmaceutically acceptable salt thereof under conditions suitable for salt formation.

In one embodiment, the compound of Formula (I) is (S)-3-(4-((4-(morpholinomethyl)benzyl)oxy)-1-oxoisoindolin-2-yl)piperidine-2,6-dione.
In one embodiment, R is $C_{1-6}$ alkyl; $C_{3-6}$ cycloalkyl; $C_{1-6}$ haloalkyl; $C_{2-10}$ heteroalkyl; $C_{3-6}$ heterocycloalkyl; $C_{1-6}$ alkyl or $C_{2-10}$ heteroalkyl substituted with 1 to 3 aryl; or —$SiR^a_3$ wherein each $R^a$ is independently $C_{1-6}$ alkyl or $C_{5-14}$ aryl.
In one embodiment, R is methyl, ethyl, propyl, isopropyl, cyclopropyl, butyl, isobutyl, tert-butyl, methoxymethyl (MOM), methylthiomethyl (MTM), tetrahydropyranyl (THP), methoxyethoxymethyl (MEM), 2-(trimethylsilyl)ethoxymethylamine (SEM), benzyloxymethyl (BOM), 2-(trimethylsilyl)ethyl (TMSE), 2,2,2-trichloroethyl, benzyl, triphenylmethyl, p-methoxybenzyl, 2,6-dimethoxybenzyl, trimethylsilyl (TMS), triethylsilyl (TES), triisopropylsilyl (TIPS), dimethylisopropylsilyl (IPDMS), diethylisopropylsilyl (DEIPS), t-butyldimethylsilyl (TBDMS), or t-butyldiphenylsilyl (TBDPS). In one embodiment, R is methyl, tert-butyl, or benzyl. In one embodiment, R is methyl. In another embodiment, R is tert-butyl. In yet another embodiment, R is benzyl.
In one embodiment, Y is hydrogen.
In one embodiment, Y is a suitable amino protecting group. In one embodiment, Y is allyl, t-butyl, methoxymethyl (MOM), methylthiomethyl (MTM), benzyloxymethyl (BOM), 2,2,2-trichloroethoxymethyl, t-butyldimethylsiloxymethyl, pivaloyloxymethyl, cyanomethyl, pyrrolidinomethyl, methoxy, benzyloxy, methylthio, triphenylmethylthio, t-butyldimethylsilyl (TBDMS), triisopropylsilyl (TIPS), 4-methoxyphenyl, 4-(methyoxymethoxy)phenyl, 2-methoxy-1-naphthyl, benzyl, 4-methoxybenzyl, 2,4-dimethoxybenzyl, 3,4-dimethoxybenzyl, 2-acetoxy-4-methoxybenzyl, 2-nitrobenzyl, bis(4-methoxyphenyl)methyl (DAM), bis(4-methoxyphenyl)phenylmethyl, bis(4-methylsulfinylphenyl)methyl, triphenylmethyl (Tr), 9-phenylfluorenyl (Pf), bis(trimethylsilyl)methyl, t-butoxycarbonyl (BOC), benzyloxycarbonyl (Cbz), methoxycarbonyl, ethoxycarbonyl, p-toluenesulfonyl (Ts), butenyl, (E)-2-(methoxycarbonyl)vinyl, diethoxymethyl, 1-methoxy-2,2-dimethylpropyl, or 2-(4-methylphenylsulfonyl)ethyl. In one embodiment, Y is benzyl, 4-methoxybenzyl, t-butyldimethylsilyl, t-butoxycarbonyl, or benzyloxycarbonyl. In one embodiment, Y is benzyl.
In one embodiment, step 1.a occurs by hydrogenation. In one embodiment, R is benzyl, and step 1.a occurs by hydrogenation.
In one embodiment, step 1.a occurs in the presence of a base. In one embodiment, step 1.a occurs in the presence of an alkali metal hydroxide, carbonate, hydrogencarbonate, phosphate, hydrogenphosphate, or dihydrogenphosphate. In one embodiment, step 1.a occurs in the presence of LiOH, NaOH, KOH, $Na_2CO_3$, $K_2CO_3$, $Cs_2CO_3$, $NaHCO_3$, $KHCO_3$, $Na_3PO_4$, $K_3PO_4$, $Na_2HPO_4$, $K_2HPO_4$, $NaH_2PO_4$, or $KH_2PO_4$. In one embodiment, R is methyl, and step 1.a occurs in the presence of NaOH or KOH.
In one embodiment, step 1.a occurs in the presence of M-$R^c$ or M-$OR^c$, wherein M is alkali metal; and $R^c$ is substituted or unsubstituted $C_{1-10}$ alkyl. In one embodiment, step 1.a occurs in the presence of sodium methoxide, sodium ethoxide, sodium t-butoxide, potassium methoxide, potassium ethoxide, or potassium t-butoxide. In one embodiment, R is methyl, and step 1.a occurs in the presence of sodium tert-butoxide, or potassium tert-butoxide.
In one embodiment, step 1.a occurs in the presence of an acid. In some embodiments, the acid is generated in situ. In one embodiment, step 1.a occurs in the presence of an organic acid. In one embodiment, step 1.a occurs in the presence of $R^bCOOH$ wherein $R^b$ is hydrogen, substituted or unsubstituted $C_{1-10}$ alkyl, substituted or unsubstituted $C_{1-10}$ haloalkyl, or substituted or unsubstituted $C_{5-14}$ aryl. In one embodiment, step 1.a occurs in the presence of formic acid, acetic acid, trifluoroacetic acid, or benzoic acid. In one embodiment, R is tert-butyl, and step 1.a occurs in the presence of trifluoroacetic acid.

In one embodiment, step 1.a occurs in the presence of $R^bSO_3H$ wherein $R^b$ is hydrogen, substituted or unsubstituted $C_{1-10}$ alkyl, substituted or unsubstituted $C_{1-10}$ haloalkyl, or substituted or unsubstituted $C_{5-14}$ aryl. In one embodiment, step 1.a occurs in the presence of sulfonic acid, benzenesulfonic acid, p-toluenesulfonic acid, camphorsulfonic acid, methanesulfonic acid, or trifluoromethanesulfonic acid. In one embodiment, step 1.a occurs in the presence of benzenesulfonic acid, p-toluenesulfonic acid, camphorsulfonic acid, or methanesulfonic acid. In one embodiment, step 1.a occurs in the presence of benzenesulfonic acid. In another embodiment, step 1.a occurs in the presence of p-toluenesulfonic acid. In yet another embodiment, step 1.a occurs in the presence of camphorsulfonic acid. In yet another embodiment, step 1.a occurs in the presence of methanesulfonic acid. In one embodiment, R is tert-butyl, and step 1.a occurs in the presence of benzenesulfonic acid.

In one embodiment, step 1.a occurs in the presence of an inorganic acid. In one embodiment, step 1.a occurs in the presence of hydrochloric acid, sulfuric acid, nitric acid, or phosphoric acid. In one embodiment, step 1.a occurs in the presence of hydrochloric acid. In one embodiment, R is tert-butyl, and step 1.a occurs in the presence of hydrochloric acid.

Step 1.a may occur in any solvent or any combination of solvents. In some embodiments, the solvent is, or the combination of solvents contains, diethyl ether, 1,4-dioxane, tetrahydrofuran, ethyl acetate, isopropyl acetate, acetonitrile, methanol, ethanol, isopropyl alcohol, dimethylformamide, dimethyl sulfoxide, glyme, diglyme, dimethylacetamide, or N-methyl-2-pyrrolidone. In some embodiments, the solvent is acetonitrile.

Step 1.a may occur at any reaction temperature. In some embodiments, the reaction temperature is from about −100° C. to about 200° C. In some embodiments, the reaction temperature is from about −50° C. to about 150° C. In some embodiments, the reaction temperature is from about 0° C. to about 100° C. In some embodiments, the reaction temperature is from about 85° C. to about 95° C. In some embodiments, the reaction temperature is about 90° C.

Step 1.a may occur at any reaction time. In some embodiments, the reaction time is from about 1 minute to about 14 days. In some embodiments, the reaction time is from about 5 minute to about 48 hours. In some embodiments, the reaction time is from about 1 hour to about 24 hours. In some embodiments, the reaction time is from about 3 hours to about 12 hours. In some embodiments, the reaction time is from about 8 hours to about 9 hours.

Step 1.4 is as described above and herein.

6.2.2 Preparation of Compound (II)

In one embodiment, as depicted in Scheme 2 below, provided herein is a process for preparing an enantiomerically enriched or enantiomerically pure compound of Formula (II), or a salt thereof, comprising:

(step 2) contacting an enantiomerically enriched or enantiomerically pure compound of Formula (IV) with a compound with Formula (V), or a salt thereof, wherein $Z^1$ and $Z^2$ are as defined above and herein; and L is halogen, $-OSO_2CH_3$, $-OSO_2CF_3$, $-OSO_2CCl_3$, $-OSO_2CH_2CF_3$, $-OSO_2CH_2CCl_3$, $-OSO_2C_6H_4$-p-Me (para-toluenesulfonate), or a suitable leaving group; under conditions suitable for displacement.

Scheme 2

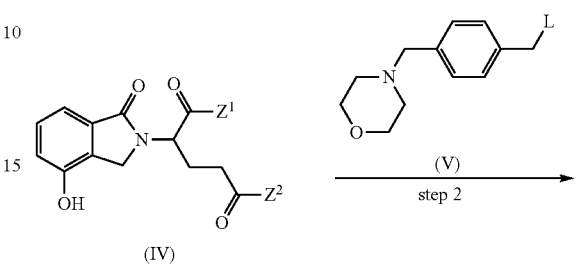

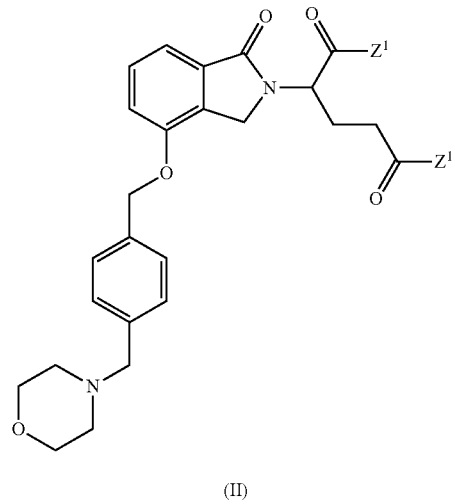

(i) $Z^1$ is NHY, and $Z^2$ is OR; or
(ii) $Z^1$ is OR, and $Z^2$ is NHY

L may be any suitable leaving group known to those of ordinary skill in the art. In one embodiment, L is halogen, $-OSO_2CH_3$, $-OSO_2CF_3$, $-OSO_2CCl_3$, $-OSO_2CH_2CF_3$, $-OSO_2CH_2CCl_3$, or $-OSO_2C_6H_4$-p-Me (para-toluenesulfonate). In one embodiment, L is halogen. In one embodiment, L is fluoro. In another embodiment, L is chloro. In yet another embodiment, L is bromo. In yet another embodiment, L is iodo.

$Z^1$, $Z^2$, R, and Y are as defined above and herein. The selection of R group is important for step 2. A sterically hindered R group, such as tert-butyl, generally results in higher conversion of a compound of Formula (IV) to a compound of Formula (II), than a non-sterically hindered R group, such as methyl, does.

The displacement of the leaving group L with the phenol group in a compound of Formula (IV) (step 2) may occur in the presence of a base. In some embodiments, the base is generated in situ. In one embodiment, step 2 occurs in the presence of an alkali metal base. In one embodiment, step 2 occurs in the presence of an alkali metal hydroxide, carbonate, hydrogencarbonate, phosphate, hydrogenphosphate, or dihydrogenphosphate. In one embodiment, step 2 occurs in the presence of LiOH, NaOH, KOH, $Na_2CO_3$, $K_2CO_3$, $Cs_2CO_3$, $NaHCO_3$, $KHCO_3$, $Na_3PO_4$, $K_3PO_4$, $Na_2HPO_4$, $K_2HPO_4$, $NaH_2PO_4$, or $KH_2PO_4$. In one embodiment, step 2 occurs in the presence of $K_2CO_3$.

In one embodiment, step 2 occurs in the presence of M-$R^c$ or M-$OR^c$, wherein M is alkali metal; and $R^c$ is substituted or unsubstituted $C_{1-10}$ alkyl. In one embodiment, step 2 occurs in the presence of sodium methoxide, sodium ethoxide, sodium t-butoxide, potassium methoxide, potassium ethoxide, or potassium t-butoxide.

In one embodiment, step 2 occurs in the presence of a nitrogen containing base. In one embodiment, step 2 occurs in the presence of triethylamine, diisopropylethylamine, pyridine, 4-dimethylaminopyridine, or 1,8-diazabicyclo[5.4.0]undec-7-ene (DBU).

Step 2 may occur in any solvent or any combination of solvents. In some embodiments, the solvent is, or the combination of solvents contains, diethyl ether, 1,4-dioxane, tetrahydrofuran, ethyl acetate, isopropyl acetate, acetonitrile, methanol, ethanol, isopropyl alcohol, dimethylformamide, dimethyl sulfoxide, glyme, diglyme, dimethylacetamide, or N-methyl-2-pyrrolidone. In one embodiment, the solvent is acetonitrile. In another embodiments, the solvent is dimethylformamide.

Step 2 may occur at any reaction temperature. In some embodiments, the reaction temperature is from about −100° C. to about 200° C. In some embodiments, the reaction temperature is from about −50° C. to about 150° C. In some embodiments, the reaction temperature is from about 0° C. to about 100° C. In some embodiments, the reaction temperature is from about 40° C. to about 50° C.

Step 2 may occur at any reaction time. In some embodiments, the reaction time is from about 1 minute to about 14 days. In some embodiments, the reaction time is from about 5 minute to about 48 hours. In some embodiments, the reaction time is from about 1 hour to about 24 hours. In some embodiments, the reaction time is from about 12 hours to about 24 hours.

Step 2 may occur at any molar ratio of the compound of Formula (IV) to the compound of Formula (V). In some embodiments, the molar ratio of the compound of Formula (IV) to the compound of Formula (V) is from about 10:1 to about 1:10. In some embodiments, the molar ratio of the compound of Formula (IV) to the compound of Formula (V) is from about 5:1 to about 1:5. In some embodiments, the molar ratio of the compound of Formula (IV) to the compound of Formula (V) is from about 3:1 to about 1:3. In some embodiments, the molar ratio of the compound of Formula (IV) to the compound of Formula (V) is from about 1.5:1 to about 1:1.5. In some embodiments, the molar ratio of the compound of Formula (IV) to the compound of Formula (V) is from about 1.1:1 to about 1:1.1. In some embodiments, the molar ratio of the compound of Formula (IV) to the compound of Formula (V) is about 1:1.

In one embodiment, Y is hydrogen, R is tert-butyl and L is chloro. In one embodiment, Y is hydrogen, R is tert-butyl and L is chloro, wherein step 2 occurs in the presence of $K_2CO_3$. In one exemplary embodiment, Y is hydrogen, R is tert-butyl and L is chloro, wherein step 2 occurs in the presence of $K_2CO_3$, the solvent is dimethylformamide, the reaction temperature is from about 40° C. to about 50° C., the reaction time is from about 12 hours to about 24 hours, and the molar ratio of the compound of Formula (IV) to the compound of Formula (V) is about 1:1.

The formation of the ether linkage in a compound of Formula (II) may be achieved by other chemical transformations known to those of ordinary skill in the art. For example, a Mitsunobu reaction between a compound of Formula (IV), in its racemic form, and an alcohol of Formula (B), in the presence of diisopropyl azodicarboxylate (DIAD) and $PPh_3$, has been reported in U.S. Patent Publication No. 2011/0196150.

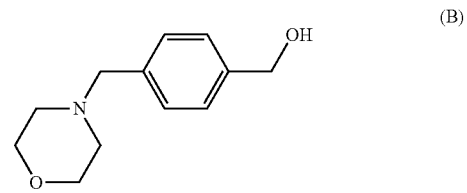

(B)

Silica gel chromatography is often required for the purification of coupling product of a Mitsunobu reaction. The basic displacement process as depicted in Scheme 2 has the following advantages over the reported Mitsunobu reaction: (1) efficient and scalable; (2) high conversion; and (3) simple purification without the need of silica gel chromatography.

6.2.3 Preparation of Compound (V)

In one embodiment, as depicted in Scheme 3 below, provided herein is a process for preparing a compound of Formula (V), or a salt thereof, comprising:
(step 3.1) contacting a compound of Formula (VI), wherein each L is independently halogen, —$OSO_2CH_3$, —$OSO_2CF_3$, —$OSO_2CCl_3$, —$OSO_2CH_2CF_3$, —$OSO_2CH_2CCl_3$, —$OSO_2C_6H_4$-p-Me (para-toluenesulfonate), or a suitable leaving group;
with morpholine, or a salt thereof, under conditions suitable for displacement; and
(step 3.2) optionally purifying the compound of Formula (V) by selective extraction.

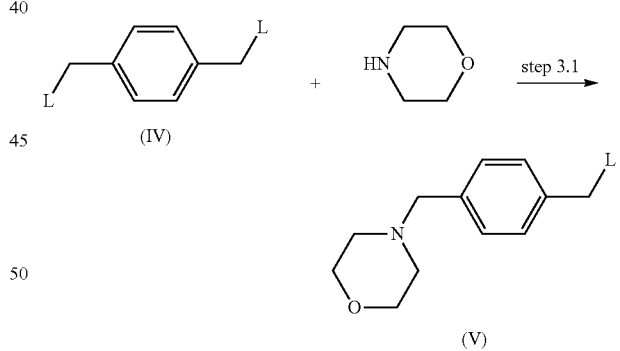

Scheme 3

Each L independently may be any suitable leaving group known to those of ordinary skill in the art. In one embodiment, each L is independently halogen, —$OSO_2CH_3$, —$OSO_2CF_3$, —$OSO_2CCl_3$, —$OSO_2CH_2CF_3$, —$OSO_2CH_2CCl_3$, or —$OSO_2C_6H_4$-p-Me (para-toluenesulfonate). In one embodiment, each L is independently halogen. In one embodiment, both L are chloro. In another embodiment, one L is chloro and the other L is —$OSO_2Me$.

The displacement of the leaving group L with morpholine (step 3.1) may occur in the presence of a base. In some embodiments, the base is generated in situ. In one embodiment, step 3.1 occurs in the presence of an alkali metal base. In one embodiment, step 3.1 occurs in the presence of an alkali metal hydroxide, carbonate, hydrogencarbonate, phosphate, hydrogenphosphate, or dihydrogenphosphate. In one embodiment, step 3.1 occurs in the presence of LiOH, NaOH, KOH, Na$_2$CO$_3$, K$_2$CO$_3$, Cs$_2$CO$_3$, NaHCO$_3$, KHCO$_3$, Na$_3$PO$_4$, K$_3$PO$_4$, Na$_2$HPO$_4$, K$_2$HPO$_4$, NaH$_2$PO$_4$, or KH$_2$PO$_4$.

In one embodiment, step 3.1 occurs in the presence of M-R$^c$ or M-OR$^c$, wherein M is alkali metal; and R$^c$ is substituted or unsubstituted C$_{1-10}$ alkyl. In one embodiment, step 3.1 occurs in the presence of sodium methoxide, sodium ethoxide, sodium t-butoxide, potassium methoxide, potassium ethoxide, or potassium t-butoxide.

In one embodiment, step 3.1 occurs in the presence of a nitrogen containing base. In one embodiment, step 3.1 occurs in the presence of triethylamine, diisopropylethylamine, pyridine, 4-dimethylaminopyridine, or 1,8-diazabicyclo[5.4.0]undec-7-ene (DBU). In one embodiment, step 3.1 occurs in the presence of diisoprorylethylamine. In another embodiment, morpholine itself serves as the base.

Step 3.1 may occur in any solvent or any combination of solvents. In some embodiments, the solvent is, or the combination of solvents contains, diethyl ether, 1,4-dioxane, tetrahydrofuran, ethyl acetate, isopropyl acetate, acetonitrile, methanol, ethanol, isopropyl alcohol, dimethylformamide, dimethyl sulfoxide, glyme, diglyme, dimethylacetamide, or N-methyl-2-pyrrolidone. In one embodiment, the solvent is acetonitrile. In another embodiment, the solvent is tetrahydrofuran. In yet another embodiment, the solvent is isopropyl acetate.

The reaction temperature, reaction time and molar ratio of the compound of Formula (VI) to morpholine are important to achieve the optimal conversion of the compound of Formula (V). In certain cases, elevated reaction temperature, prolonged reaction time, and/or large excess of morpholine may result in the formation of a large amount of by-product 1,4-bis(morpholinomethyl)benzene or a salt thereof.

Step 3.1 may occur at any reaction temperature. In some embodiments, the reaction temperature is from about −100° C. to about 200° C. In some embodiments, the reaction temperature is from about −50° C. to about 150° C. In some embodiments, the reaction temperature is from about 0° C. to about 100° C. In some embodiments, the reaction temperature is about room temperature.

Step 3.1 may occur at any reaction time. In some embodiments, the reaction time is from about 1 minute to about 14 days. In some embodiments, the reaction time is from about 5 minute to about 48 hours. In some embodiments, the reaction time is from about 1 hour to about 24 hours. In some embodiments, the reaction time is from about 20 hours to no more than 24 hours.

Step 3.1 may occur at any molar ratio of the compound of Formula (VI) to morpholine. In some embodiments, the molar ratio of the compound of Formula (VI) to morpholine is from about 10:1 to about 1:10. In some embodiments, the molar ratio of the compound of Formula (VI) to morpholine is from about 5:1 to about 1:5. In some embodiments, the molar ratio of the compound of Formula (VI) to morpholine is from about 3:1 to about 1:3. In some embodiments, the molar ratio of the compound of Formula (VI) to morpholine is from about 1.5:1 to about 1:1.5. In one embodiment, the molar ratio of the compound of Formula (VI) to morpholine is about 1:1.5. In another embodiment, the molar ratio of the compound of Formula (VI) to morpholine is about 1:1.

Step 3.1 usually results in a mixture of the compound of Formula (V), or a salt thereof, and by-product 1,4-bis(morpholinomethyl)benzene, or a salt thereof. The mixture may be optionally separated by selective extraction in a suitable solvent or a combination of suitable solvents (step 3.2). In some embodiments, the solvent is, or the combination of solvents contains, diethyl ether, 1,4-dioxane, tetrahydrofuran, ethyl acetate, isopropyl acetate, acetonitrile, methanol, ethanol, isopropyl alcohol, dimethylformamide, dimethyl sulfoxide, glyme, diglyme, dimethylacetamide, or N-methyl-2-pyrrolidone. In one embodiment, the solvent is methanol.

In one exemplary embodiment, both L are chloro, wherein step 3.1 occurs in a solvent of isopropyl acetate, the reaction temperature is about room temperature, the reaction time is from about 20 hours to no more than 24 hours, and the molar ratio of the compound of Formula (VI) to morpholine is about 1:1.5; and the compound of Formula (V) is optionally purified by selective extraction in methanol.

In another exemplary embodiment, one L is chloro, and the other L is —OSO$_2$CH$_3$, wherein step 3.1 occurs in the presence of diisopropylethylamine and the solvent is acetonitrile.

6.2.4 Preparation of Compound (IV)

The compound of Formula (IV) may be prepared using methods known to those of ordinary skill in the art. For example, the preparation of a compound of Formula (IV), wherein R is methyl and the compound is in its racemic form, has been reported in U.S. Patent Publication No. 2011/0196150.

In one embodiment, provided herein is a process for preparing an enantiomerically enriched or enantiomerically pure compound of Formula (IV), comprising
(step 4) deprotecting an enantiomerically enriched or enantiomerically pure compound of Formula (VII):

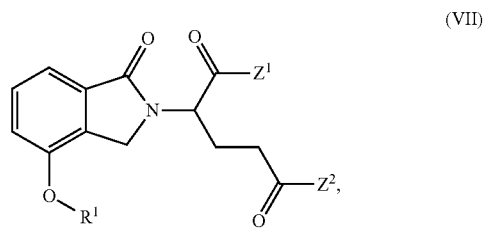

wherein
(i) Z$^1$ is NHY, and Z$^2$ is OR; or
(ii) Z$^1$ is OR, and Z$^2$ is NHY; and
R$^1$ is a suitable phenol protecting group;
under conditions suitable for deprotection.

Suitable phenol protecting groups are well known to those of ordinary skill in the art. The choice and use of protecting groups and the reaction conditions to install and remove protecting groups are described in T. W. Green, *Protective Groups in Organic Synthesis* (Third Ed., Wiley, New York, 1999). In one embodiments, R$^1$ is methyl, isopropyl, cyclopropylmethyl, tert-butyl, cyclohexyl, allyl, propargyl, cyanomethyl, 2-bromoethyl, methoxymethyl (MOM), methylthiomethyl (MTM), methoxyethoxymethyl (MEM), 2-(trimethylsilyl)ethoxymethylamine (SEM), tetrahydropyranyl (THP), benzyl, p-methoxybenzyl, 2,6-dimethoxybenzyl, 2,6-dichlorobenzyl, trimethylsilyl (TMS), triethylsilyl (TES), triisopropylsilyl (TIPS), dimethylisopropylsilyl (IPDMS), diethylisopropylsilyl (DEIPS), t-butyldimethylsilyl (TBDMS), or t-butyldiphenylsilyl (TBDPS), formate, acetate, benzoate, methyl carbonate, t-butyl carbonate (BOC), benzyl carbonate, dimethylphosphinyl, methanesulfonate, or toluenesulfonate.

In one exemplary embodiment, Y is hydrogen, R is tert-butyl and $R^1$ is t-butyldimethylsilyl (TBDMS), wherein the reaction occurs in methanol in the presence of tetrabutylammonium fluoride (TBAF).

6.2.5 Preparation of Compound (VII)

The compound of Formula (VII) may be prepared using methods known to those of ordinary skill in the art. For example, the preparation of a compound of Formula (VII), wherein R is methyl, $R^1$ is t-butyldimethylsilyl (TBDMS), and the compound is in its racemic form, has been reported in U.S. Patent Publication No. 2011/0196150.

In one embodiment, provided herein is a process for preparing an enantiomerically enriched or enantiomerically pure compound of Formula (VII), comprising
(step 5) contacting a compound of Formula (VIII):

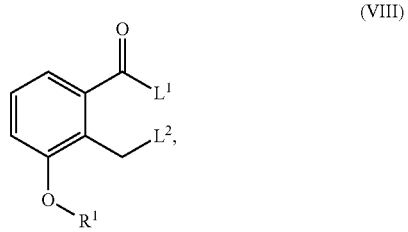

wherein
$R^1$ is a suitable phenol protecting group; $L^1$ and $L^2$ are, independently, halogen, $OR^2$, $OCOR^2$, $OSO_2R^2$, $OPO_3R^2$, or a suitable leaving group;
wherein $R^2$ is saturated, partially saturated, or unsaturated $C_{1-10}$ alkyl, optionally substituted with one or more halogen; or 5 to 10 membered aryl or heteroaryl, optionally substituted with one or more halogen;
with an enantiomerically enriched or enantiomerically pure compound of Formula (IX), or a salt thereof:

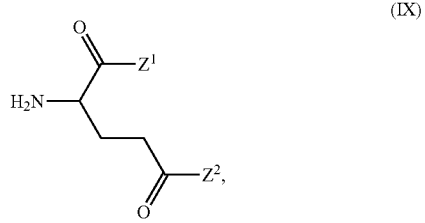

wherein
(i) $Z^1$ is NHY, and $Z^2$ is OR; or
(ii) $Z^1$ is OR, and $Z^2$ is NHY;
under conditions suitable for cyclization.

$L^1$ and $L^2$ may be, independently, any suitable leaving group known to those of ordinary skill in the art. In one embodiment, $L^1$ and $L^2$ are, independently, halogen, methoxy, $-OSO_2CH_3$, $-OSO_2CF_3$, $-OSO_2CCl_3$, $-OSO_2CH_2CF_3$, $-OSO_2CH_2CCl_3$, or $-OSO_2C_6H_4$-p-Me (para-toluenesulfonate). In one embodiment, $L^1$ is methoxy, and $L^2$ is bromo.

In one exemplary embodiment, Y is hydrogen, R is tert-butyl, $R^1$ is t-butyldimethylsilyl (TBDMS), $L^1$ is methoxy, and $L^2$ is bromo, wherein the reaction occurs in acetonitrile in the presence of $KH_2PO_4$.

In another exemplary embodiment, Y is hydrogen, R is methyl, $R^1$ is t-butyldimethylsilyl (TBDMS), $L^1$ is methoxy, and $L^2$ is bromo, wherein the reaction occurs in acetonitrile in the presence of diisopropylethylamine.

6.2.6 Preparation of Compound (VIII)

The compound of Formula (VIII) may be prepared using methods known to those of ordinary skill in the art. For example, the preparation of a compound of Formula (VIII), wherein $R^1$ is t-butyldimethylsilyl, $L^1$ is methoxy, and $L^2$ is bromo, has been reported in U.S. Patent Publication No. 2011/0196150.

In one embodiment, provided herein is a process for preparing a compound of Formula (VIII), comprising
(step 6) halogenating a compound of Formula (X) at its benzylic position:

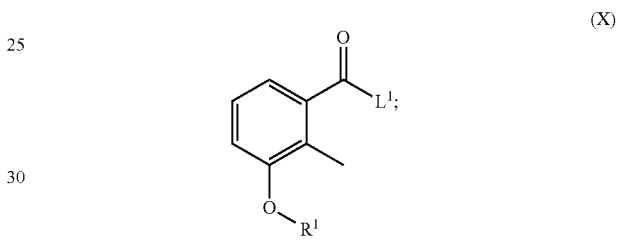

under conditions suitable for halogenations.

In one embodiment, the halogenation reaction is free radical bromination. The free radical bromination may be initiated by ultraviolet radiation, sunlight, or heating in the presence of a radical initiator. The bromination reagents and conditions for free radical bromination are well known to those of ordinary skill in the art. In one exemplary embodiment, the bromination reagent is 1-bromopyrrolidine-2,5-dione (NBS), the radical initiator is 2,2'-(diazene-1,2-diyl)bis(2-methylpropanenitrile) (AIBN), and the solvent is isopropyl acetate.

6.2.7 Preparation of Compound (X)

The compound of Formula (X) may be prepared using methods known to those of ordinary skill in the art. For example, the preparation of a compound of Formula (X), wherein $R^1$ is t-butyldimethylsilyl, and $L^1$ is methoxy, has been reported in U.S. Patent Publication No. 2011/0196150.

In one embodiment, provided herein is a process for preparing a compound of Formula (X), comprising
(step 7) reacting a compound of Formula (XI):

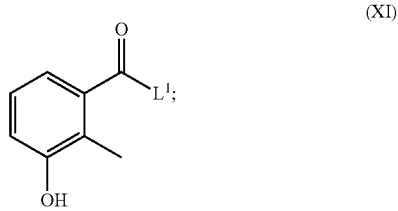

with a protecting group under conditions suitable for protection.

In one exemplary embodiment, $L^1$ is methoxy, wherein the protection occurs in a solvent of N,N-diemethylformamide, and in the presence of tert-butyldimethylsilyl chloride and imidazole.

6.2.8 Preparation of Compound (XI)

The compound of Formula (XI) may be prepared using methods known to those of ordinary skill in the art. For example, the preparation of a compound of Formula (XI), wherein $L^1$ is methoxy, has been reported in U.S. Patent Publication No. 2011/0196150.

In one embodiment, provided herein is a process for preparing a compound of Formula (XI), comprising
(step 8) reacting 3-hydroxy-2-methylbenzoic acid with an alcohol under conditions suitable for esterification.

The methods for preparing an ester from an acid are well known to those of ordinary skill in the art. In some embodiments, the esterification occurs by reacting the acid with an alcohol under an acidic condition. In one exemplary embodiment, the alcohol is methanol and the reaction occurs in the presence of sulfuric acid.

6.2.9 ADDITIONAL EMBODIMENTS

In one embodiment, provided herein is a process for preparing an enantiomerically enriched or enantiomerically pure (S)-3-(4-((4-(morpholinomethyl)benzyl)oxy)-1-oxoisoindolin-2-yl)piperidine-2,6-dione, wherein Y is hydrogen, R is tert-butyl, and step 1.1 and step 1.2 occur in one-pot in the presence of benzenesulfonic acid; wherein L is chloro, and step 2 occurs in the presence of $K_2CO_3$.

In one embodiment, provided herein is a process for preparing an enantiomerically enriched or enantiomerically pure (S)-3-(4-((4-(morpholinomethyl)benzyl)oxy)-1-oxoisoindolin-2-yl)piperidine-2,6-dione, wherein Y is hydrogen, R is tert-butyl, and step 1.1 and step 1.2 occur in one-pot in the presence of benzenesulfonic acid; wherein L is chloro, and step 2 occurs in the presence of $K_2CO_3$; wherein step 3.1 occurs in a solvent of isopropyl acetate, the reaction temperature is about room temperature, the reaction time is from about 20 hours to no more than 24 hours, and the molar ratio of the compound of Formula (VI) to morpholine is about 1:1.5; and the compound of Formula (V) is optionally purified by selective extraction in methanol.

In one embodiment, provided herein is a process for preparing an enantiomerically enriched or enantiomerically pure (S)-3-(4-((4-(morpholinomethyl)benzyl)oxy)-1-oxoisoindolin-2-yl)piperidine-2,6-dione, wherein Y is hydrogen, R is tert-butyl, and step 1.1 and step 1.2 occur in one-pot in the presence of benzenesulfonic acid; wherein L is chloro, and step 2 occurs in the presence of $K_2CO_3$; wherein $R^1$ is t-butyldimethylsilyl (TBDMS), step 4 occurs in methanol in the presence of tetrabutylammonium fluoride (TBAF).

In one embodiment, provided herein is a process for preparing an enantiomerically enriched or enantiomerically pure (S)-3-(4-((4-(morpholinomethyl)benzyl)oxy)-1-oxoisoindolin-2-yl)piperidine-2,6-dione, or a pharmaceutically acceptable form thereof, comprising:
(step 1.1) transforming an enantiomerically enriched or enantiomerically pure compound of Formula (II), or a salt thereof, to an enantiomerically enriched or enantiomerically pure compound of Formula (III), or a salt thereof, under conditions suitable for ester to acid transformation;
(step 1.2) cyclizing the enantiomerically enriched or enantiomerically pure compound of Formula (III) to an enantiomerically enriched or enantiomerically pure compound of Formula (I-a) under conditions suitable for cyclization;
(step 1.3) where Y is not hydrogen, deprotecting the enantiomerically enriched or enantiomerically pure compound of Formula (I-a) to an enantiomerically enriched or enantiomerically pure compound of Formula (I) under conditions suitable for deprotection; and
(step 1.4) optionally transforming the enantiomerically enriched or enantiomerically pure compound of Formula (I) to a pharmaceutically acceptable salt thereof under conditions suitable for salt formation;
wherein step 1.1 and step 1.2 occur in one-pot; and
wherein the enantiomerically enriched or enantiomerically pure compound of Formula (II) is prepared by a process comprising:
(step 2) contacting an enantiomerically enriched or enantiomerically pure compound of Formula (IV) with a compound with Formula (V), or a salt thereof, under conditions suitable for displacement;
wherein the compound of Formula (V) is prepared by a process comprising:
(step 3.1) contacting a compound of Formula (VI) with morpholine, or a salt thereof, under conditions suitable for displacement; and
(step 3.2) optionally purifying the compound of Formula (V) by selective extraction;
wherein the enantiomerically enriched or enantiomerically pure compound of Formula (IV) is prepared by a process comprising:
(step 4) deprotecting an enantiomerically enriched or enantiomerically pure compound of Formula (VII) under conditions suitable for deprotection;
wherein the enantiomerically enriched or enantiomerically pure compound of Formula (VII) is prepared by a process comprising:
(step 5) contacting a compound of Formula (VIII) with an enantiomerically enriched or enantiomerically pure compound of Formula (IX), or a salt thereof, under conditions suitable for cyclization;
wherein the compound of Formula (VIII) is prepared by a process comprising:
(step 6) halogenating a compound of Formula (X) at its benzylic position under conditions suitable for halogenation;
wherein the compound of Formula (X) is prepared by a process comprising:
(step 7) reacting a compound of Formula (XI) with a protecting group under conditions suitable for protection;
wherein the compound of Formula (XI) is prepared by a process comprising:
(step 8) reacting 3-hydroxy-2-methylbenzoic acid with an alcohol under conditions suitable for esterification;
wherein R, $R^1$, $R^2$, Y, L, $L^1$, and $L^2$ are as defined above and herein.

All of the combinations of the above embodiments are encompassed by this invention.

It is to be understood that the processes of the present invention are also suitable for the preparation of the R-enantiomer or racemate of 3-(4-((4-(morpholinomethyl) benzyl)oxy)-1-oxoisoindolin-2-yl)piperidine-2,6-dione, via replacing the compound of Formula (IX) with its corresponding R-enantiomer or racemate. Additionally, the racemate of 3-(4-((4-(morpholinomethyl)benzyl)oxy)-1-oxoisoindolin-2-yl)piperidine-2,6-dione may be synthesized by the racemization of any enantiomerically enriched or pure compounds on the synthetic route according to methods known in the art and provided herein.

6.3 Enhancement of Enantiopurity

In one embodiment, provided herein are methods of increasing the enantiopurity of a compound of Formula (I), or a salt and/or solvate thereof. Generally, enantiopurity can be increased by recrystallization or trituration under conditions that lead to optimal $ee_{eu}$.

In one embodiment, provided herein is a process for increasing or enhancing the enantiopurity of (S)-3-(4-((4-(morpholinomethyl)benzyl)oxy)-1-oxoisoindolin-2-yl)piperidine-2,6-dione, or a salt and/or solvate thereof, comprising recrystallization or trituration of a first sample of (S)-3-(4-((4-(morpholinomethyl)benzyl)oxy)-1-oxoisoindolin-2-yl)piperidine-2,6-dione, or a salt and/or solvate thereof, in a solvent or a mixture of solvents, resulting in a second sample of (S)-3-(4-((4-(morpholinomethyl)benzyl)oxy)-1-oxoisoindolin-2-yl)piperidine-2,6-dione, or a salt and/or solvate thereof, wherein the second sample has a higher ee than the first sample.

In one embodiment, the enantiopurity is increased by recrystallization. In another embodiment, the enantiopurity is increased by trituration.

In one embodiment, the enantiopurity may increase by 1%, 5%, 10%, 15%, 20%, 25%, 30% or more after the recrystallization or trituration as compared to the enantiopurity before the recrystallization or trituration.

The first sample of (S)-3-(4-((4-(morpholinomethyl)benzyl)oxy)-1-oxoisoindolin-2-yl)piperidine-2,6-dione (i.e., the sample whose enantiopurity is to be increased) may be in anhydrous form, freebase form, hydrate form, solvate form, salt form, or any combination thereof. In one embodiment, the first sample is in the anhydrous freebase form. In another embodiment, the first sample is in the freebase hydrate form. In another embodiment, the first sample is in the freebase THF solvate form. In yet another embodiment, the first sample is in the HCl salt form. In yet another preferred embodiment, the first sample is in the anhydrous HCl salt form.

The ee of the first sample may be from 0% to about 95%. In one embodiment, the ee of the first sample is from about 25% to about 90%. In one embodiment, the ee of the first sample is from about 50% to about 80%. In one embodiment, the ee of the first sample is about 75%.

The recrystallization or trituration may occur in any solvent or any combination of solvents. In some embodiments, the solvent is, or the combination of solvents contains, water, diethyl ether, 1,4-dioxane, tetrahydrofuran, ethyl acetate, isopropyl acetate, acetonitrile, methanol, ethanol, isopropyl alcohol, dimethylformamide, dimethyl sulfoxide, glyme, diglyme, dimethylacetamide, or N-methyl-2-pyrrolidone. In one embodiment, the solvent is acetonitrile. In another embodiment, the solvent is tetrahydrofuran.

In one embodiment, the solvent is an alcohol. In one embodiment, the solvent is methanol.

In one embodiment, the solvent is a mixture of alcohol and water. In one embodiment, the solvent is a mixture of isopropyl alcohol and water. In one embodiment, the solvent is a 90:10 mixture of isopropyl alcohol and water. In another embodiment, the solvent is a 95:5 mixture of isopropyl alcohol and water.

The recrystallization or trituration may occur at any temperature. In some embodiments, the temperature is from about 0° C. to about 100° C. In some embodiments, the temperature is from about 10° C. to about 80° C. In one embodiment, the temperature is about 22° C. In another embodiment, the temperature is about 55° C.

The second sample of (S)-3-(4-((4-(morpholinomethyl)benzyl)oxy)-1-oxoisoindolin-2-yl)piperidine-2,6-dione (i.e., the compound after increase of enantiopurity) may be in a same or different form as that of the first sample of (S)-3-(4-((4-(morpholinomethyl)benzyl)oxy)-1-oxoisoindolin-2-yl)piperidine-2,6-dione. In one embodiment, the second sample is in a different form as that of the first sample. In another embodiment, the second sample is in a same form as that of the first sample. In one embodiment, both the first and the second samples are in the HCl salt form.

The ee of the second sample is higher than the ee of the first sample. In one embodiment, the ee of the second sample is no less than about 50%, no less than about 60%, no less than about 70%, no less than about 80%, no less than about 85%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, no less than about 99.9%, no less than about 99.95%, no less than about 99.99%, or about 100%.

In one embodiment, the first sample of (S)-3-(4-((4-(morpholinomethyl)benzyl)oxy)-1-oxoisoindolin-2-yl)piperidine-2,6-dione is in the HCl salt form having an ee of 75%, the trituration occurs in methanol at 55° C., resulting in a second sample of (S)-3-(4-((4-(morpholinomethyl)benzyl)oxy)-1-oxoisoindolin-2-yl)piperidine-2,6-dione in the HCl salt form having an ee of 97.5%.

All of the combinations of the above embodiments are encompassed by this invention.

7. EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); µL (microliters); M (molar); mM (millimolar); µM (micromolar); eq. (equivalent); mmol (millimoles); Hz (Hertz); MHz (megahertz); hr or hrs (hour or hours); min (minutes); and MS (mass spectrometry). Unless otherwise specified, the water content in a compound provided herein is determined by Karl Fisher (KF) method.

For all of the following examples, unless otherwise specified, standard work-up and purification methods known to those skilled in the art can be utilized. Unless otherwise specified, all temperatures are expressed in ° C. (degrees Centigrade). All reactions were conducted at room temperature unless otherwise noted. Synthetic methodologies illustrated herein are intended to exemplify the applicable chemistry through the use of specific examples and are not indicative of the scope of the disclosure.

Example 1

Synthesis of methyl 2-(bromomethyl)-3-((tert-butyldimethylsilyl)oxy)benzoate

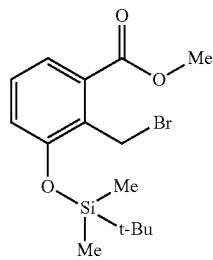 [SMILES: COC(=O)c1cccc(O[Si](C)(C)C(C)(C)C)c1CBr]

Step 1:

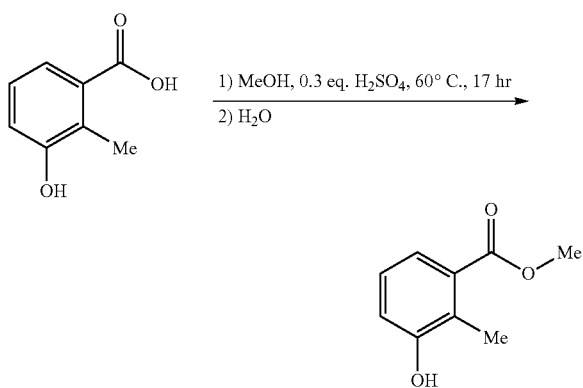

3-Hydroxy-2-methylbenzoic acid (250 g, 1.32 mole) was added to methanol (2500 mL, 10×) in a jacketed bottom drop three neck flask under nitrogen. Sulfuric acid (48.3 g, 0.49 mole) was added to the above solution. The mixture was heated to 60° C. and stirred for 8 to 17 hours. Once conversion was >98%, the mixture was atmospherically distilled to 3× volume. The residue was cooled to 20° C. and slowly added to water (500 mL, 2×) over at least 30 minutes. Seeds (2 g, 0.01×) were added and the mixture was agitated at 20° C. for at least 1 hour. Water (1500 mL, 6×) was added at 20° C. over at least 3 hours and the mixture was agitated at 20° C. for at least one additional hour. The solid was filtered, and washed three times with 9:1 water:methanol (500 mL, 2× each) until pH≥3. The solid was dried under vacuum at 35 to 45° C. until KF≤0.1% to give methyl 3-hydroxy-2-methylbenzoate (235.3 g, 86% yield); $^1$H NMR (DMSO-d$_6$, 300 MHz) δ 9.68 (s, 1H), 7.18 (dd, J=7.5, 1.2 Hz, 1H), 7.08 (t, J=7.5 Hz, 1H), 7.00 (dd, J=8.1, 1.2 Hz, 1H), 3.80 (s, 3H), 2.29 (s, 3H) ppm.

Step 2:

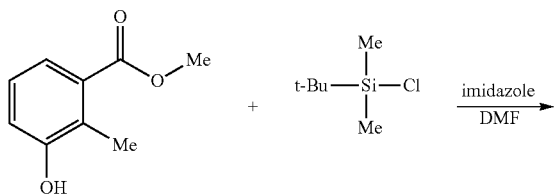

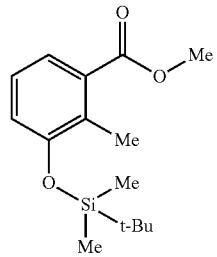

Methyl 3-hydroxy-2-methylbenzoate (110 g, 662 mmol) was added to DMF (660 mL, 6×) in a 3 liter jacketed bottom drop reactor. The mixture was cooled to 5° C., and imidazole (113 g, 1655 mmol, 1.03×) was added to the solution. tert-Butyldimethylsilyl chloride (110 g, 728 mmol, 1×) was added, and the mixture was agitated at 5° C. for 1 hour. The mixture was warmed up to 20° C. and agitated for at least 2 hours until no more than 0.2% of the starting phenol was left. Isopropyl acetate (770 mL, 7×) was added, then water (1100 mL, 10×) was slowly added, keeping temperature below 30° C. The mixture was agitated, settled, and split. The organic layer was washed three additional times with water (770 mL, 7× each), and distilled under vacuum at 40 to 55° C. to 6× volume and until KF was no more than 0.05%. The methyl 3-((tert-butyldimethylsilyl)oxy)-2-methylbenzoate product was stored as isopropyl acetate solution, which was used in the next step without further purification (expected 168 g, 90% yield); $^1$H NMR (DMSO-d$_6$, 300 MHz) δ 7.15 (dd, J=7.8, 1.2 Hz, 1H), 6.97 (t, J=7.8 Hz, 1H), 6.82 (dd, J=8.1, 1.2 Hz, 1H), 3.60 (s, 3H), 2.29 (s, 3H), 0.97 (s, 9H), 0.18 (s, 6H) ppm.

Step 3:

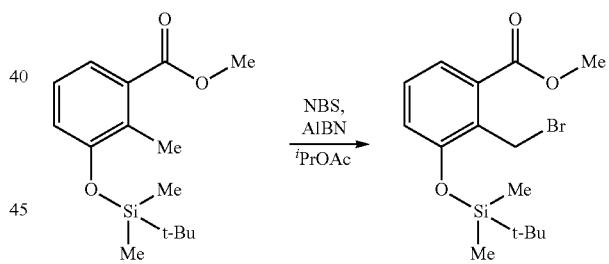

The isopropyl acetate solution of methyl 3-((tert-butyldimethylsilyl)oxy)-2-methylbenzoate (157 g, 560 mmol, from step 2, with an amount of residue free phenol ≤0.2%) was added to a 3 liter jacketed bottom drop reactor. Additional isopropyl acetate was added and the mixture was distilled under vacuum at 40 to 55° C., if necessary, to bring total volume to about 9× (1410 mL, KF≤0.05%). 1-Bromopyrrolidine-2,5-dione (NBS, 103.6 g, 580 mmol, 0.66×) and 2,2'-(diazene-1,2-diyl)bis(2-methylpropanenitrile) (AIBN, 1.9 g, 11 mmol, 0.012×) were added to the solution. The reaction mixture was heated to 70° C. over at least 2 hours and stirred at 70° C. for 2 hours. The color changed from orange to yellow. If conversion was less than 95%, additional 0.05 molar equiv. of NBS was added and the mixture was stirred at 70° C. for 1 hour. The process was repeated, in necessary, until conversion reached 95%. The mixture was cooled to 20° C. and held at 20° C. for at least 1 hour. The solid (succinimide) was filtered and washed with isopropyl acetate (75 mL, 0.5×). The filtrate was washed with solution of sodium sulfite (157 g, 1×) in water (1413 mL, 9×), followed by water (315 mL, 2×). The organic layer was distilled under vacuum at 30 to 40° C. to ~2× volume. Additional isopropyl acetate (315 mL, 2×) was added and distilled back to 2× volume, if necessary, until KF was no more than 0.1%. Then the organic layer was distilled at 30 to 40° C. to give methyl 2-(bromomethyl)-3-((tert-butyldimethylsilyl)oxy)benzoate as an oil (expected 180 g, 90% yield); $^1$H NMR (DMSO-$d_6$, 300 MHz) δ 7.47 (dd, J=7.8, 1.2 Hz, 1H), 7.37 (t, J=8.1 Hz, 1H), 7.15 (dd, J=8.1, 1.2 Hz, 1H), 4.96 (s, 2H), 3.86 (s, 3H), 1.03 (s, 9H), 0.30 (s, 6H) ppm.

Example 2

Synthesis of (S)-tert-butyl 5-amino-4-(4-hydroxy-1-oxoisoindolin-2-yl)-5-oxopentanoate

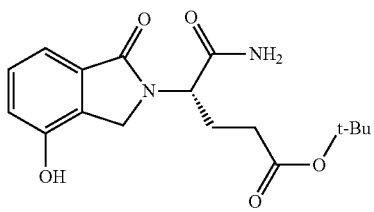 [SMILES: CC(C)(C)OC(=O)CC[C@@H](C(N)=O)N1Cc2c(O)cccc2C1=O]

Step 1:

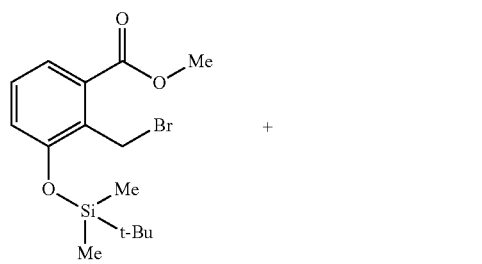

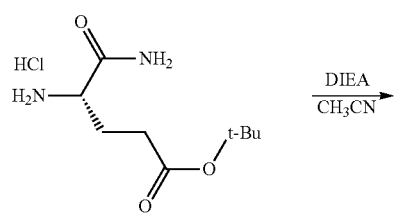

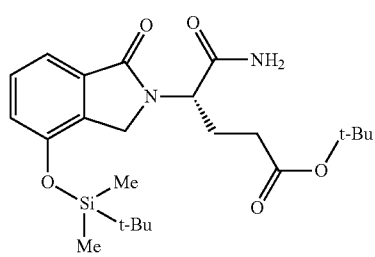

Methyl 2-(bromomethyl)-3-((tert-butyldimethylsilyl)oxy) benzoate (250 g, 696 mmol) and (S)-tert-butyl 4,5-diamino-5-oxopentanoate hydrochloride (183 g, 765 mmol) were added to acetonitrile (2150 mL, 8.6×) in a 5 liter jacketed bottom drop vessel with overhead agitation under nitrogen. Diisopropylethylamine (DIEA, 303 mL, 1.74 mmol, 1.2×) was added, and the mixture was heated at 45 to 50° C. for 24 to 45 hours. Once conversion was ≥97%, the mixture was distilled under vacuum below 50° C. to 4× volume. An aqueous wash solution of $KH_2PO_4$ (190 g, 1.32 mmol, 0.75×) in water (2500 mL, 10×) was prepared in a separate vessel. The reaction mixture was cooled to 20 to 25° C., and methyl tert-butyl ether (MTBE, 1500 mL, 6×) was added. The mixture was washed twice with half of the phosphate solution and twice with water (500 mL, 2×). The mixture was atmospherically distilled to 4× volume (1000 mL). Additional MTBE was added and the mixture was distilled back to 4× volume, if necessary, until KF was ≤0.2%. Methanol (1500 mL, 6×) was then added, and the mixture was distilled under vacuum at 25 to 35° C. to 4× volume. Additional methanol was added and the mixture was distilled back to 4× volume, if necessary, until MTBE was no more than 5% with respect to methanol by mole). The crude (S)-tert-butyl 5-amino-4-(4-((tert-butyldimethylsilyl)oxy)-1-oxoisoindolin-2-yl)-5-oxopentanoate was used in the next step without further purification.

Step 2:

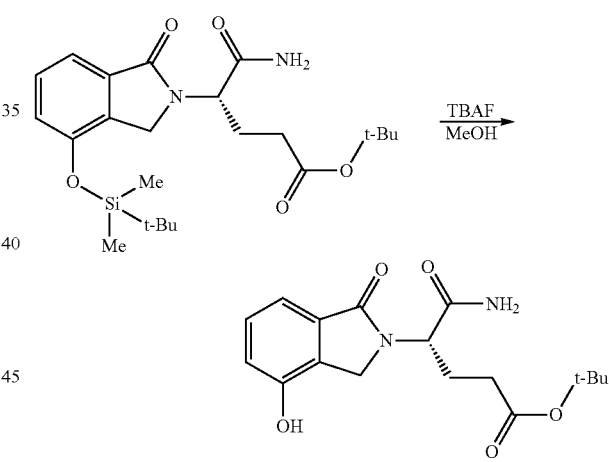

Methanol (1500 mL, 6×) was added to the crude (S)-tert-butyl 5-amino-4-(4-((tert-butyldimethylsilyl)oxy)-1-oxoisoindolin-2-yl)-5-oxopentanoate from step 1. Tetrabutylammonium fluoride trihydrate (35 g, 0.14×) was added. The mixture was agitated at 15 to 25° C. for 12 to 24 hours. The agitation was prolonged, if necessary, until conversion reached 99.5%. The mixture was distilled under vacuum below 45° C. to 3.5 to 4× volume (875 to 1000 mL). Baffle was inserted into the reactor, the temperature was adjusted to 15 to 25° C., and seeds (1.25 g, 0.005×) were added. Water (1750 mL, 7×) was added over 7 hours. The mixture was agitated for 12 to 24 hours. The solid was filtered, washed with water (500 mL, 2×), and dried under reduced pressure with nitrogen bleed at 40° C. until KF≤0.5%. The crude (S)-tert-butyl 5-amino-4-(4-hydroxy-1-oxoisoindolin-2-yl)-5-oxopentanoate was used in the next step without further purification.

Step 3:

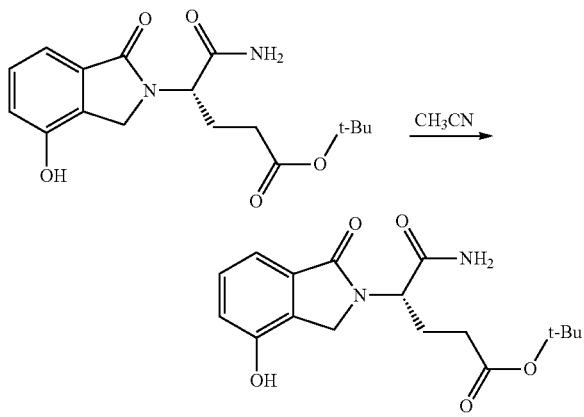

The crude (S)-tert-butyl 5-amino-4-(4-hydroxy-1-oxoisoindolin-2-yl)-5-oxopentanoate from step 2 was added to acetonitrile (750 mL, 3×) in a 2 liter flask with overhead agitation, thermocouple and nitrogen atmosphere. The mixture was heated to 60 to 70° C. and agitated in this range for 4 to 5 hours. The mixture was cooled to 15 to 25° C. over 4 to 5 hours and agitated in this range for 12 to 24 hours. The solid was filtered, washed with acetonitrile (250 mL, 1×), and dried under reduced pressure with nitrogen sweep at 35 to 45° C. until Loss On Drying (LOD)≤1% to give (S)-tert-butyl 5-amino-4-(4-hydroxy-1-oxoisoindolin-2-yl)-5-oxopentanoate (182 g, 78% yield); MS m/z: 335.1 (M+1); $^1$H NMR (DMSO-d$_6$, 300 MHz) δ 10.03 (s, 1H), 7.56 (br s, 1H), 7.31 (dd, J=7.8, 7.8 Hz, 1H), 7.18 (br s, 1H), 7.15 (dd, J=7.5, 0.6 Hz, 1H), 6.98 (dd, J=7.8, 0.6 Hz, 1H), 4.71 (dd, J=10.2, 4.2 Hz, 1H), 4.49 (d, J=17.7 Hz, 1H), 4.32 (d, J=17.4 Hz, 1H), 2.21-1.93 (m, 4H), 1.34 (s, 9H) ppm.

Example 3

Synthesis of 4-(4-(chloromethyl)benzyl)morpholine hydrochloride

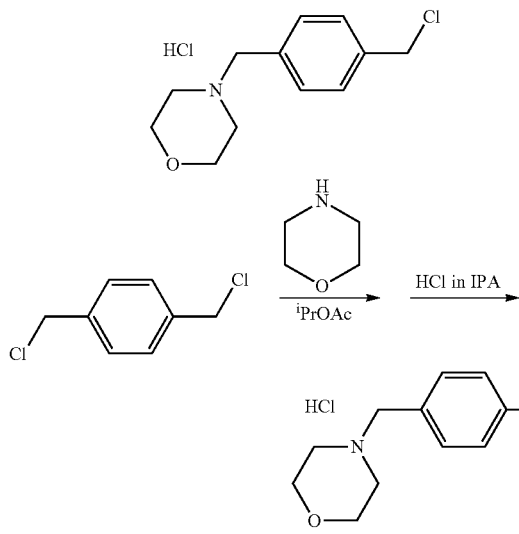

1,4-Bis(chloromethyl)benzene (50 g, 286 mmol) was added to isopropyl acetate (500 mL, 10×) in a reaction vessel. Once the solid dissolved, morpholine (37.5 mL, 428 mmol) was added in a single portion. The mixture was stirred at room temperature for 20 to no more than 24 hours. The solid (morpholine-HCl and bis-morpholine by-product) was filtered and washed with isopropyl acetate (50 mL). The filtrate was washed twice with water (125 mL) and once with 5% brine (100 mL). The organic phase was dried azeotropically or with MgSO$_4$. HCl in 2-propanol (IPA, 50 mL, 5-6 N) was added to the dried organic phase. The first 20 mL was added slowly to establish a good seed bed. The resulting white solid was filtered, washed with isopropyl acetate (100 mL), dried on the filter to constant weight to give crude product (39.4 g, including 80.3% strength product and 19.7% bis-morpholine by-product, 56.4% yield).

The crude product (2.0 g, 80.3% strength, 48.8 mmol) was added to methanol (20 mL, 10×), and the mixture was stirred at room temperature for 3 hours. The solid (bis-morpholine by-product) was filtered and NOT rinsed. Isopropyl acetate (20 mL) was added to the filtrate, and methanol was removed by distillation at atmospheric pressure. Methanol removal was considered sufficiently complete when the head temperature dropped rapidly from the boiling temperature of methanol (64-65° C.). The mixture was cooled to room temperature and stirred overnight. The resulting solid was filtered by rapid vacuum filtration, washed with isopropyl acetate (1-2 mL), dried on funnel over vacuum to constant weight, to give 4-(4-(chloromethyl)benzyl)morpholine hydrochloride as a white crystal product (1.3 g, 81% yield); MS m/z: 226.1, 228.0 (M+1); $^1$H NMR (DMSO-d$_6$, 300 MHz) δ 11.56 (br s, 1H), 7.65 (d, J=8.1 Hz, 2H), 7.51 (d, J=8.1 Hz, 2H), 4.79 (s, 2H), 4.32 (d, J=5.4 Hz, 2H), 3.94-3.78 (m, 4H), 3.20-3.00 (m, 4H) ppm; $^{13}$C NMR (DMSO-d$_6$, 75 MHz) δ 138.9, 131.8, 129.3, 129.1, 63.0, 58.4, 50.6, 45.5 ppm.

Example 4

Synthesis of (S)-tert-butyl 5-amino-4-(4-((4-(morpholinomethyl)benzyl)oxy)-1-oxoisoindolin-2-yl)-5-oxopentanoate

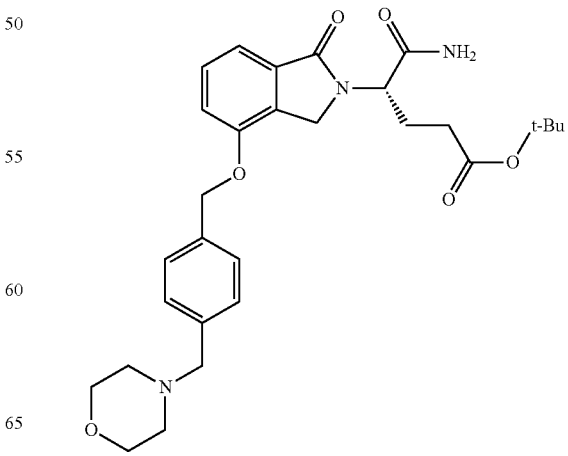

-continued

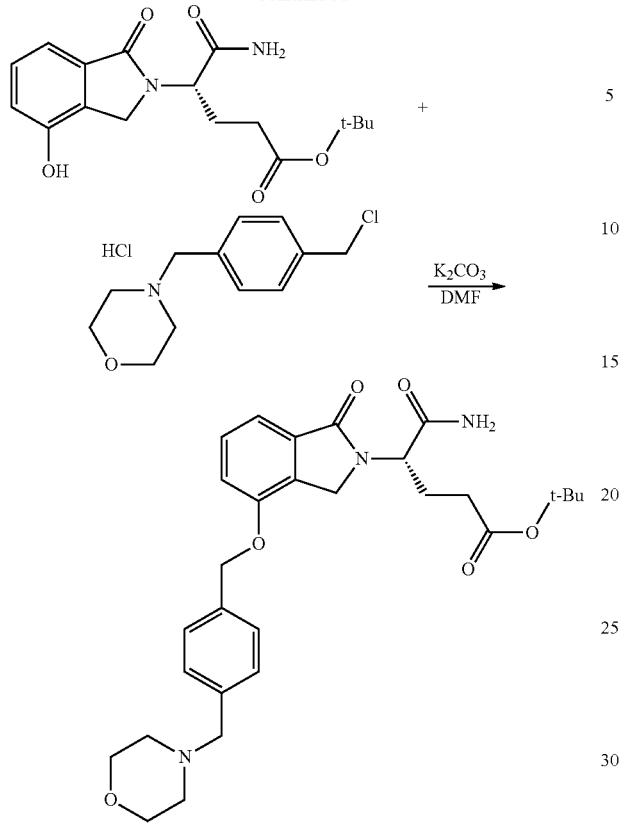

(S)-tert-Butyl 5-amino-4-(4-hydroxy-1-oxoisoindolin-2-yl)-5-oxopentanoate (160 g), 4-(4-(chloromethyl)benzyl)morpholine hydrochloride (138 g, 0.87×) and potassium carbonate (165 g, 1.04×) were added to DMF (960 mL, 6×) in a 5 liter jacketed vessel. The mixture was heated to 40 to 50° C. and agitated for 12 to 24 hours. The mixture was cooled to 25 to 35° C., then ethyl acetate (1600 mL, 10×) and water (1600 mL, 10×) were added. The mixture was agitated at 25 to 35° C., settled, and split. Additional ethyl acetate (800 mL, 5×) and water (800 mL, 5×) were added. The mixture was agitated at 25 to 35° C., settled, and split. The combined organic phase was washed four times with water (400 mL, 2.5×). The organic phase was distilled under vacuum below 50° C. to 6× volume. Additional ethyl acetate (2880 mL, 18×) was continuously added, and the distillation was continued to maintain about 6× volume. The temperature was adjusted to 40 to 45° C., then seeds (0.8 g, 0.005×) were added. The mixture was held for about 30 minutes to build seed bed, then heptane (960 mL, 6×) was added over about 1.5 hours. The mixture was cooled to 15 to 25° C. over about 1 to 1.5 hours, agitated at 15 to 25° C. for at least one hour, and held for 16 hours. The solid was filtered, washed with heptane: ethyl acetate (5× total, 2.5× heptane, 2.5× ethyl acetate), and dried under reduced pressure with nitrogen sweep at 35 to 45° C. until LOD≤1%, to give (S)-tert-butyl 5-amino-4-(4-((4-(morpholinomethyl)benzyl)oxy)-1-oxoisoindolin-2-yl)-5-oxopentanoate as a white solid (215.3 g, 86% yield); MS m/z: 524.3 (M+1); $^1$H NMR (DMSO-d$_6$, 300 MHz) δ 7.57 (br s, 1H), 7.48-7.43 (m, 3H), 7.34 (d, J=8.1 Hz, 2H), 7.29 (d, J=7.5 Hz, 2H), 7.19 (br s, 1H), 5.21 (s, 2H), 4.71 (dd, J=10.2, 4.2 Hz, 1H), 4.54 (d, J=17.4 Hz, 1H), 4.40 (d, J=17.7 Hz, 1H), 3.56 (dd, J=4.5, 4.5 Hz, 4H), 3.45 (s, 2H), 2.34 (dd, J=4.5, 4.5 Hz, 4H), 2.15-1.99 (m, 4H), 1.32 (s, 9H) ppm; $^{13}$C NMR (DMSO-d$_6$, 75 MHz) δ 171.8, 171.3, 167.8, 153.4, 137.7, 135.3, 133.3, 130.2, 129.5, 129.0, 127.6, 115.1, 114.6, 79.7, 69.4, 66.2, 62.1, 53.5, 53.1, 44.8, 31.8, 27.6, 24.8 ppm.

Example 5

Synthesis of (S)-3-(4-((4-(morpholinomethyl)benzyl)oxy)-1-oxoisoindolin-2-yl)piperidine-2,6-dione besylate

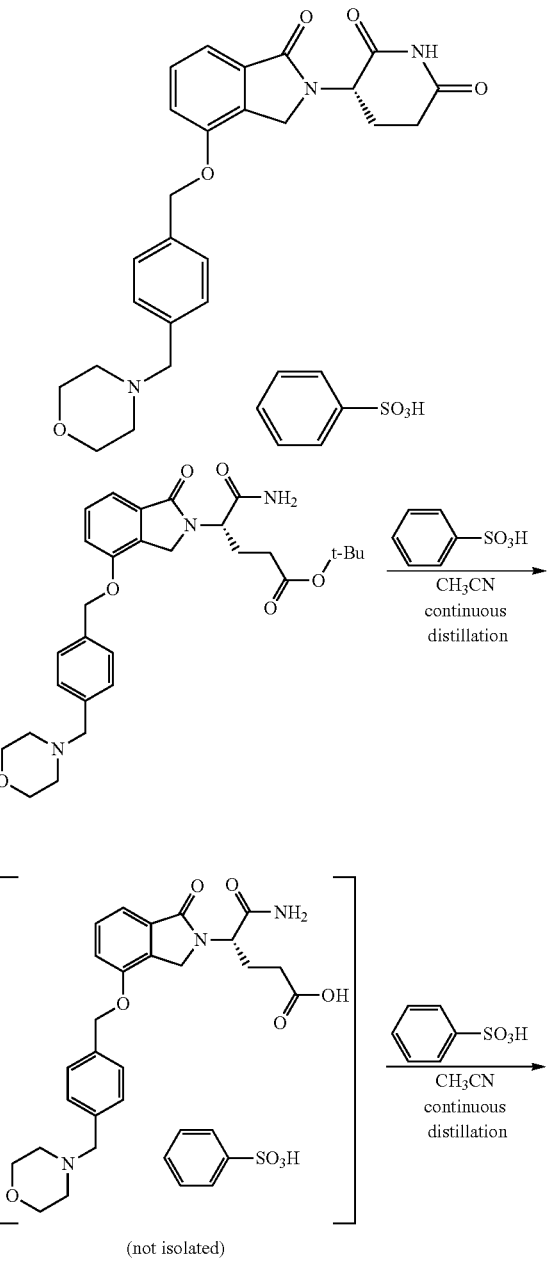

49

-continued

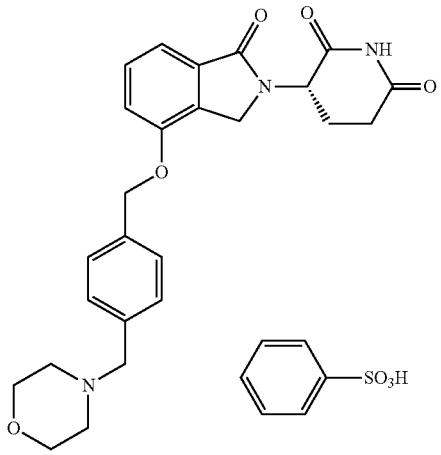

Benzenesulfonic acid (68.7 g, 0.39×) was added to acetonitrile (1400 mL, 8×) in a 5 liter jacketed flask equipped with overhead agitation, thermocouple, addition funnel, and a Dean Stark trap with condenser, with nitrogen flowing from the addition funnel, over the reaction, and out the condenser. The mixture was atmospherically continuously distilled with acetonitrile, if necessary, until KF≤0.1%. (S)-tert-Butyl 5-amino-4-(4-((4-(morpholinomethyl)benzyl) oxy)-1-oxoisoindolin-2-yl)-5-oxopentanoate (175 g, 1×) was then added. The mixture was distilled at 90° C. at a rate of 1 to 3× volume of acetonitrile per hour for 4 hours. Seeds (1.75 g, 0.01×, as a slurry in 17.5 mL of acetonitrile) were added. The mixture was continuously distilled at a rate of 1 to 3× volume of acetonitrile per hour for 4 to 5 additional hours (8 to 9 hours total). The mixture was cooled to 15 to 25° C. over about 1 to 4 hours, and agitated at 15 to 25° C. for at least 1 hour. The solid was filtered, washed with acetonitrile (350 mL, 2×), and dried under reduced pressure at 35 to 50° C. with nitrogen bleed, to give (S)-3-(4-((4-(morpholinomethyl)benzyl)oxy)-1-oxoisoindolin-2-yl)piperidine-2,6-dione besylate as a white solid (169.1 g, 83% yield); MS m/z: 450.3 (M+1); $^1$H NMR (DMSO-$d_6$, 300 MHz) δ 10.98 (s, 1H), 9.74 (br s, 1H), 7.61-7.56 (m, 4H), 7.53 (d, J=7.8 Hz, 2H), 7.48 (d, J=7.8 Hz, 1H), 7.53-7.26 (m, 5H), 5.31 (s, 2H), 5.12 (dd, J=13.2, 5.1 Hz, 1H), 4.44 (d, J=17.4 Hz, 1H), 4.37 (br d, J=4.8 Hz, 2H), 4.27 (d, J=17.4 Hz, 1H), 3.96 (br d, J=12.6 Hz, 2H), 3.61 (br dd, J=11.4, 11.4 Hz, 2H), 3.26 (br d, J=12.3 Hz, 2H), 3.17-3.10 (m, 2H), 2.92 (ddd, J=17.7, 13.8, 5.4 Hz, 1H), 2.59 (br d, J=16.5 Hz, 1H), 2.43 (dddd, J=17.4, 13.2, 13.2, 4.2 Hz, 1H), 2.01-1.97 (m, 1H) ppm; $^{13}$C NMR (DMSO-$d_6$, 75 MHz) δ 172.9, 171.0, 168.0, 153.3, 148.2, 138.3, 133.4, 131.5, 130.0, 129.9, 128.8, 128.5, 127.9, 127.7, 125.5, 115.4, 115.0, 69.0, 63.2, 59.0, 51.6, 50.9, 45.1, 31.2, 22.4 ppm.

50

Example 6

Synthesis of (S)-3-(4-((4-(morpholinomethyl)benzyl)oxy)-1-oxoisoindolin-2-yl)piperidine-2,6-dione hydrochloride

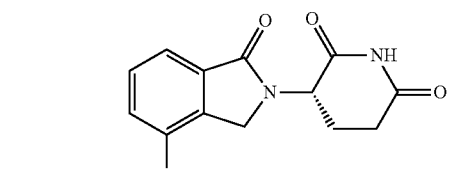

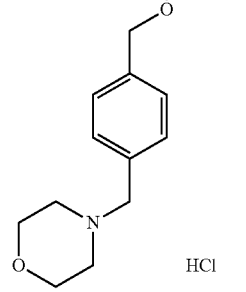

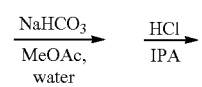

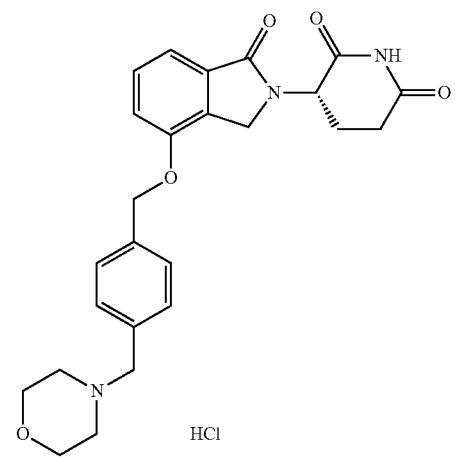

Figure 2:
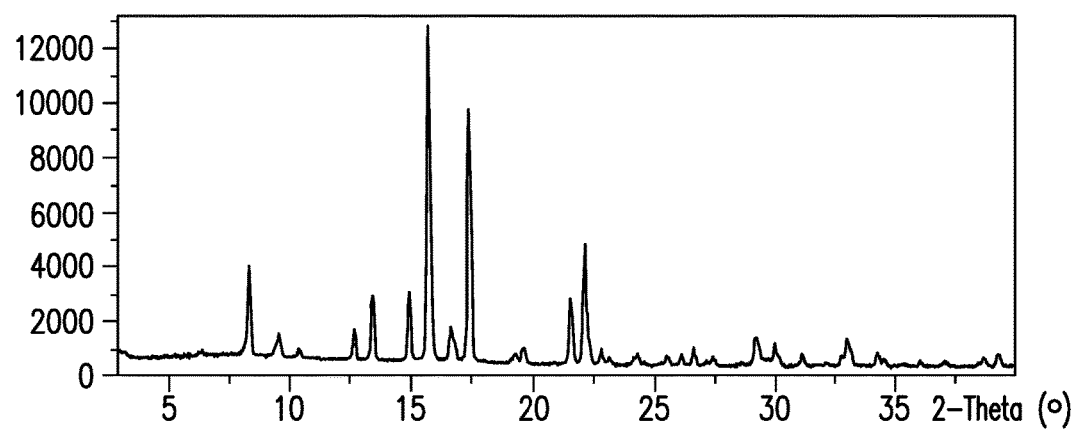
FIG. 2 depicts an X-ray powder diffractogram (XRD) of (S)-3-(4-((4-(morpholinomethyl)benzyl)oxy)-1-oxoisoindolin-2-yl)piperidine-2,6-dione hydrochloride.
Figure 3:
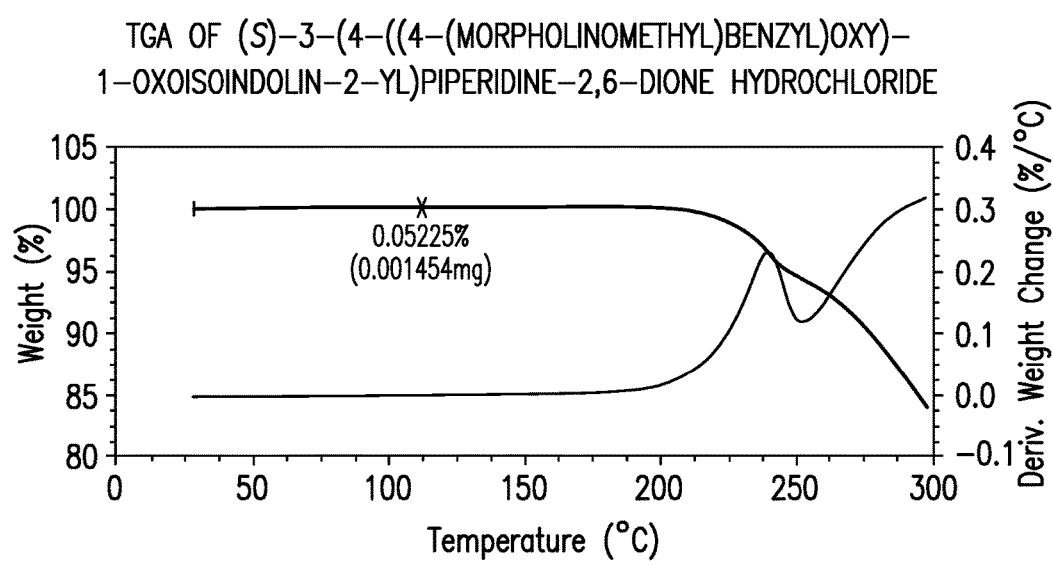
FIG. 3 depicts a thermogravimetric (TGA) thermogram of (S)-3-(4-((4-(morpholinomethyl)benzyl)oxy)-1-oxoisoindolin-2-yl)piperidine-2,6-dione hydrochloride.

(S)-3-(4-((4-(Morpholinomethyl)benzyl)oxy)-1-oxoisoindolin-2-yl)piperidine-2,6-dione besylate (75 g, 1×) and sodium bicarbonate (11.4 g, 0.15×) were added to methyl acetate (1350 mL, 18×) and water (300 mL, 4×) in a 3 liter jacketed bottom drop vessel with overhead agitation and nitrogen blanket. The mixture was agitated at 15 to 25° C. until the solid dissolved. The mixture was settled and split. Water (75 mL, 1×) was added to the organic phase, agitated for 5 minutes at 15 to 25° C., settled, and split. 6M HCl (24.7 mL, 0.33×) was added to isopropanol (IPA, 300 mL, 4×) in a separate vessel with good agitation. Seeds (1.5 g, 0.02×) were added to the HCl/IPA solution and the temperature was adjusted to 35 to 45° C. The methyl acetate solution was then added to the HCl/IPA solution over 4 to 5 hours. After addition, the mixture was agitated at 40° C. for 0.5 hour, cooled to 22° C. over 0.5 hour, and held at 22° C. overnight (~16 hours). The solid was filtered, washed twice with methyl acetate (225 mL, 3×, each time), and dried under reduced pressure with nitrogen bleed at 40° C., to give (S)-3-(4-((4-(morpholinomethyl)benzyl)oxy)-1-oxoisoindolin-2-yl)piperidine-2,6-dione hydrochloride as a white solid (48.1 g, 80% yield, 99.55% purity (HPLC), 98.3% ee); analysis for $C_{25}H_{28}ClN_3O_5$ calculated: C, 61.79; H, 5.81; N, 8.65; Cl, 7.30. found C, 61.70; H, 5.71; N, 8.58; Cl, 7.46; MS m/z: 450.2 (M+1); $^1$H NMR (DMSO-$d_6$, 300 MHz) δ 11.56 (s, 1H), 10.97 (s, 1H), 7.67 (d, J=8.1 Hz, 2H), 7.57 (d, J=8.1 Hz, 2H), 7.49 (dd, J=7.8, 7.8 Hz, 1H), 7.33 (d, J=7.8 Hz, 2H), 5.29 (s, 2H), 5.12 (dd, J=13.2, 5.1 Hz, 1H), 4.44 (d, J=17.4 Hz, 1H), 4.33 (d, J=5.4 Hz, 2H), 4.28 (d, J=17.4 Hz, 1H), 3.93-3.79 (m, 4H), 3.19 (d, J=11.7 Hz, 2H), 3.17-3.00 (m, 2H), 2.91 (ddd, J=18.9, 13.8, 5.4 Hz, 1H), 2.58 (d, J=18.3 Hz, 1H), 2.43 (dddd, J=17.4, 13.2, 13.2, 4.2 Hz, 1H), 2.02-1.95 (m, 1H) ppm; $^{13}$C NMR (DMSO-$d_6$, 75 MHz) δ 172.8, 171.0, 168.0, 153.4, 138.0, 133.4, 131.7, 130.0, 129.8, 128.9, 127.8, 115.4, 115.0, 69.0, 63.0, 58.6, 51.6, 50.6, 45.1, 31.2, 22.4 ppm; the differential scanning calorimetric (DSC) thermogram is depicted in FIG. 1; the X-ray powder diffractogram (XRD) is depicted in FIG. 2; the thermogravimetric (TGA) thermogram is depicted in FIG. 3.

Example 7

Synthesis of (S)-methyl 5-(benzylamino)-4-(4-((4-(morpholinomethyl)benzyl)oxy)-1-oxoisoindolin-2-yl)-5-oxopentanoate (S)-Methyl 5-(benzylamino)-4-(4-((4-(morpholinomethyl)benzyl)oxy)-1-oxoisoindolin-2-yl)-5-oxopentanoate is prepared under the same conditions as examples 2 and 4 by replacing (S)-tert-butyl 4,5-diamino-5-oxopentanoate hydrochloride with (S)-methyl 4-amino-5-(benzylamino)-5-oxopentanoate.

Example 8

Synthesis of (S)-1-benzyl-3-(4-((4-(morpholinomethyl)benzyl)oxy)-1-oxoisoindolin-2-yl)piperidine-2,6-dione

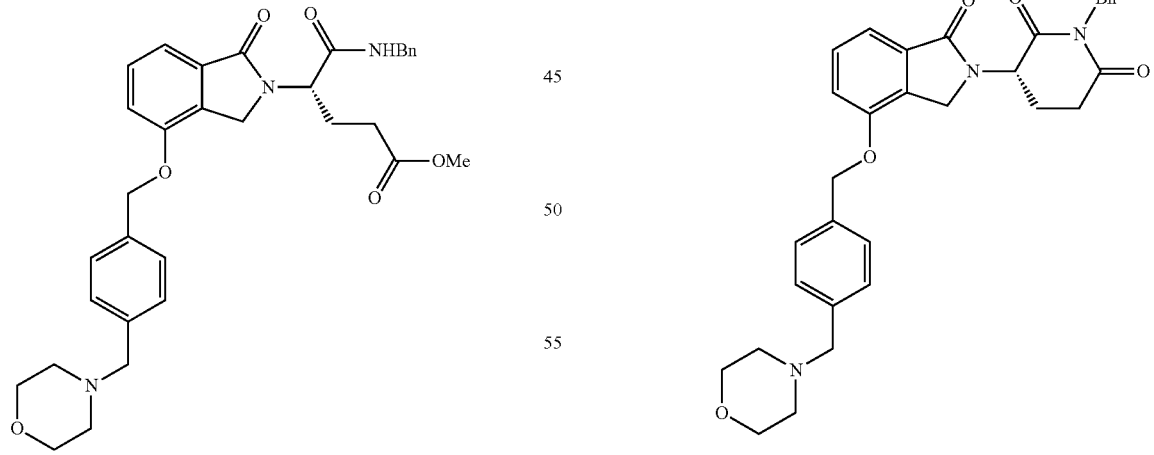

A mixture of (S)-methyl 5-(benzylamino)-4-(4-((4-(morpholinomethyl)benzyl)oxy)-1-oxoisoindolin-2-yl)-5-oxopentanoate (2.5 mmol) and p-TsOH monohydrate (1.25 mmol) in toluene, under argon, is refluxed for 8 hours. The solvent is evaporated. The crude is taken up in ether (50 mL) and washed with saturated aqueous NaHCO₃ (2×20 mL). The organic layer is dried and purified by silica gel chromatography to afford (S)-1-benzyl-3-(4-((4-(morpholinomethyl)benzyl)oxy)-1-oxoisoindolin-2-yl)piperidine-2,6-dione.

Example 9

Synthesis of (S)-3-(4-((4-(morpholinomethyl)benzyl)oxy)-1-oxoisoindolin-2-yl)piperidine-2,6-dione

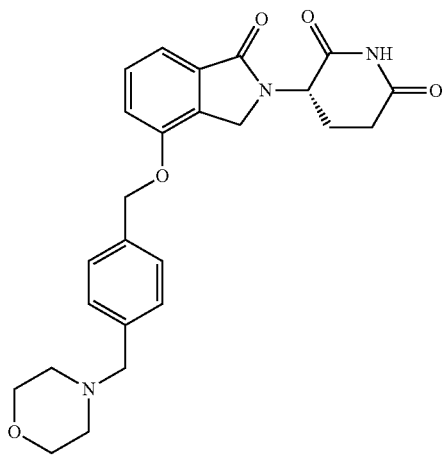 [SMILES: O=C1CC[C@H](N2Cc3c(OCc4ccc(CN5CCOCC5)cc4)cccc3C2=O)C(=O)N1]

(S)-3-(4-((4-(Morpholinomethyl)benzyl)oxy)-1-oxoisoindolin-2-yl)piperidine-2,6-dione is prepared from (S)-1-benzyl-3-(4-((4-(morpholinomethyl)benzyl)oxy)-1-oxoisoindolin-2-yl)piperidine-2,6-dione by hydrogenation in acetic acid in the presence of Pd/C for 2 days.

Example 10

Screening of conditions for enhancement of enantiopurity of (S)-3-(4-((4-(morpholinomethyl)benzyl)oxy)-1-oxoisoindolin-2-yl)piperidine-2,6-dione Initially the $ee_{eu}$ was evaluated using (S)-3-(4-((4-(morpholinomethyl)benzyl)oxy)-1-oxoisoindolin-2-yl)piperidine-2,6-dione freebase and its corresponding anhydrous freebase racemic compound in acetonitrile at 22° C., and was found to be was unfavorably high (94.7%). A hydrated form of (S)-3-(4-((4-(morpholinomethyl)benzyl)oxy)-1-oxoisoindolin-2-yl)piperidine-2,6-dione freebase was subsequently obtained, and the $ee_{eu}$ of the (S)-3-(4-((4-(morpholinomethyl)benzyl)oxy)-1-oxoisoindolin-2-yl)piperidine-2,6-dione hydrate with its corresponding hydrate racemic compound at 22° C. remained unfavorably high (89.2%). A THF solvate of (S)-3-(4-((4-(morpholinomethyl)benzyl)oxy)-1-oxoisoindolin-2-yl)piperidine-2,6-dione was also obtained, and the $ee_{eu}$ of the solvate with its corresponding anhydrate racemic compound at 22° C. was improved (68.5%). However, a THF solvate of (S)-3-(4-((4-(morpholinomethyl)benzyl)oxy)-1-oxoisoindolin-2,6-dione is not a suitable drug substance due to the toxicity of THF, and so an alternative approach was sought.

Figure 4:
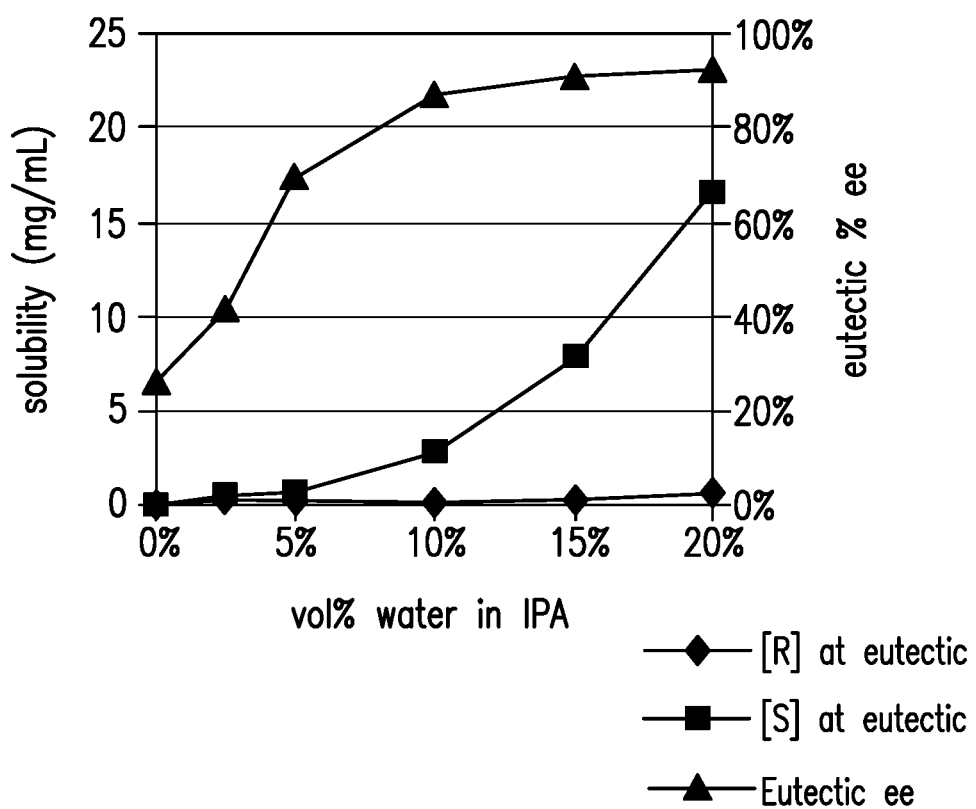
FIG. 4 depicts the eutectic solubility of the HCl salt of (S)-3-(4-((4-(morpholinomethyl)benzyl)oxy)-1-oxoisoindolin-2-yl)piperidine-2,6-dione in IPA/water.

The $ee_{eu}$ of the HCl salt of (S)-3-(4-((4-(morpholinomethyl)benzyl)oxy)-1-oxoisoindolin-2-yl)piperidine-2,6-dione and the HCl salt of the corresponding racemic compound was studied and found to be dependent on the ratio of water:co-solvent (isopropanol was used as co-solvent) at 22° C., which suggested the presence of a hydrate of either or both of the (S)-enantiomer or the racemic compound (FIG. 4). Physical characterization confirmed that the HCl salt of the racemic compound was a hydrate, which was determined to be a thermodynamically stable crystal form. The HCl salt of the single enantiomer remained as the thermodynamically stable anhydrous form. The $ee_{eu}$ at low water fractions (~5%) was favorably low (~70%) but the absolute solubility was quite low. The quantities of solvent and equipment capacity needed to provide chiral upgrade would be impractical and uneconomical. For instance, to upgrade from 90% ee to 98% ee, it was calculated to require 200 L solvent per kg starting material.

A methanol solvate of the HCl salt of racemic 3-(4-((4-(morpholinomethyl)benzyl)oxy)-1-oxoisoindolin-2-yl)piperidine-2,6-dione was subsequently produced and showed a slightly modified XRPD pattern from the corresponding hydrate. In the presence of methanol, at ambient temperature (22° C.), a favorable $ee_{eu}$ between the HCl salts of (S)-3-(4-((4-(morpholinomethyl)benzyl)oxy)-1-oxoisoindolin-2-yl)piperidine-2,6-dione and the corresponding racemic compound was achieved (72.4%). From this $ee_{eu}$, it was calculated that achieving an upgrade from 90% ee to 98% ee would require 46 L solvent per kg starting material which, while an improvement, is still undesirable.

Figure 5:
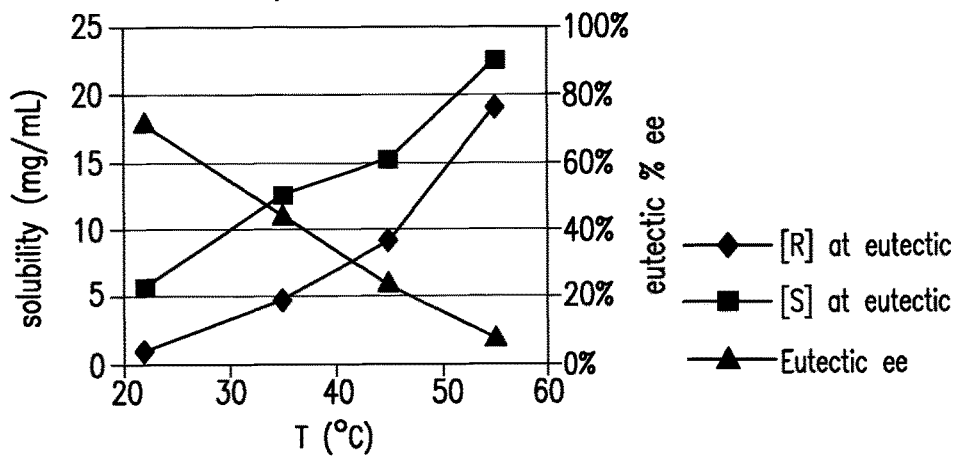
FIG. 5 depicts the eutectic solubility of the HCl salt of (S)-3-(4-((4-(morpholinomethyl)benzyl)oxy)-1-oxoisoindolin-2-yl)piperidine-2,6-dione as a function of temperature in various solvent systems.
Figure 5:
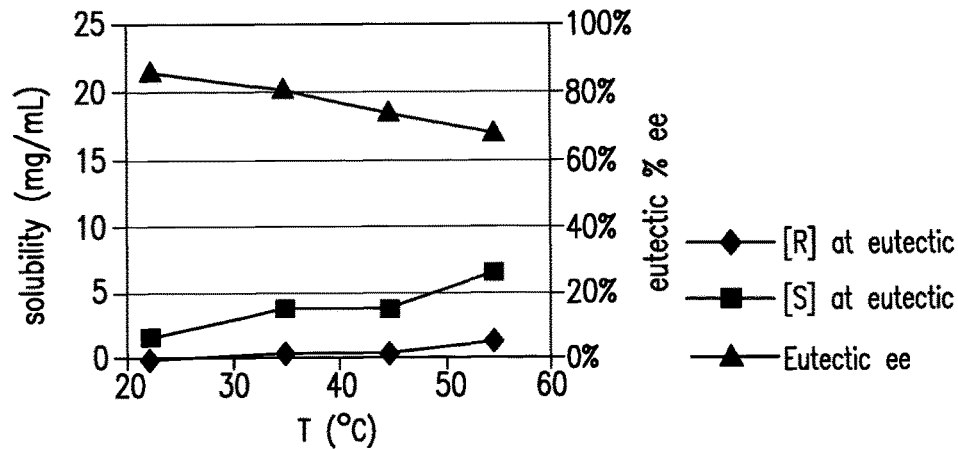
Figure 5:
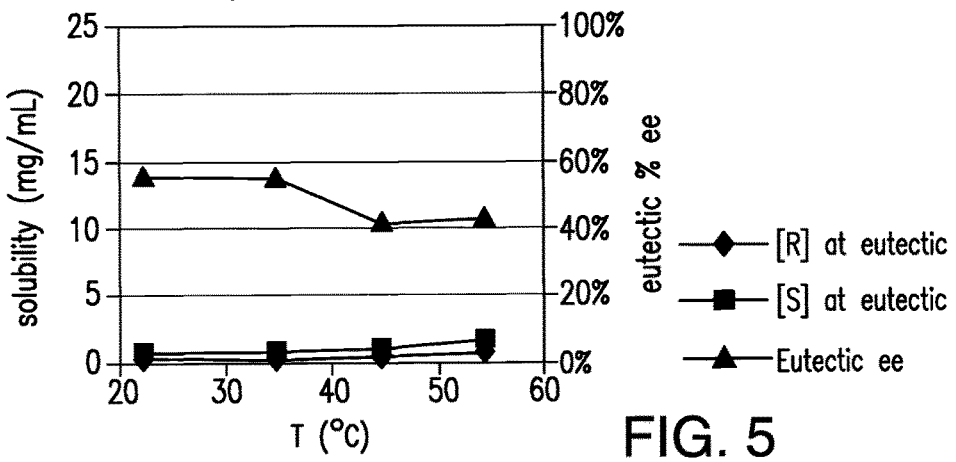

Solvated crystalline forms often have lower melting points than their anhydrous counterparts, and by extension have a relatively greater solubility as temperature is increased, relative to the corresponding anhydrate. This phenomenon was used to obtain improved $ee_{eu}$. The eutectic solubility of the HCl salt was determined as a function of temperature for neat methanol, 90/10 isopropanol/water and 95/5 isopropanol/water (FIG. 5). In all three systems, it was confirmed that $ee_{eu}$ decreased as temperature increased, as expected from the general solvate/anhydrate thermodynamic relationship.

The methanol system showed the strongest sensitivity to temperature and generally a low $ee_{eu}$. The lowest $ee_{eu}$ obtained across all crystal forms of (S)-3-(4-((4-(morpholinomethyl)benzyl)oxy)-1-oxoisoindolin-2-yl)piperidine-2,6-dione, solvents and temperatures occurred with the HCl salt in methanol at 55° C., with $ee_{eu}$=8%. Based on this result, it was calculated that to upgrade from 90% ee to 98% ee at 55° C. in methanol would require 2.1 L solvent per kg starting material, which is a vast improvement over other conditions.

Example 11

Trial run for enhancement of enantiopurity of (S)-3-(4-((4-(morpholinomethyl)benzyl)oxy)-1-oxoisoindolin-2-yl)piperidine-2,6-dione hydrochloride A crude (S)-3-(4-((4-(morpholinomethyl)benzyl)oxy)-1-oxoisoindolin-2-yl)piperidine-2,6-dione hydrochloride mixture (4 g) with 75% ee was triturated in 28 mL methanol at 55° C. for approx. 1.5 hours and then filtered at 55° C. The wet product was then washed with methanol and dried in a vacuum oven. The resulting enantiopurity of the dried product was determined to be 97.5% ee (2.5 g, 70% recovery yield of the (S)-enantiomer).

What is claimed is:
1. A process to increase the enantiopurity of (S)-3-(4-((4-(morpholinomethyl)benzyl)oxy)-1-oxoisoindolin-2-yl)piperidine-2,6-dione hydrochloride or a solvate thereof, comprising recrystallization or trituration of a first sample of (S)-3-(4-((4-(morpholinomethyl)benzyl)oxy)-1-oxoisoindo- lin-2-yl)piperidine-2,6-dione hydrochloride or a solvate thereof in methanol, resulting in a second sample of (S)-3-(4-((4-(morpholinomethyl)benzyl)oxy)-1-oxoisoindolin-2-yl)piperidine-2,6-dione hydrochloride or a solvate thereof, wherein the second sample has a higher enantiomeric excess (ee) than the first sample.

2. The process of claim 1, wherein the enantiopurity is increased by recrystallization.

3. The process of claim 1, wherein the enantiopurity is increased by trituration.

4. The process of claim 1, wherein the enantiopurity is increased by 10% or more.

5. The process of claim 4, wherein the enantiopurity is increased by 20% or more.

6. The process of claim 1, wherein the first sample is in the anhydrous HCl salt form.

7. The process of claim 1, wherein the ee of the first sample is from 25% to about 90%.

8. The process of claim 7, wherein the ee of the first sample is from 50% to about 80%.

9. The process of claim 1, wherein the recrystallization or trituration occurs at a temperature of from about 10° C. to about 80° C.

10. The process of claim 1, wherein the ee of the second sample is no less than about 90%.

11. The process of claim 10, wherein the ee of the second sample is no less than about 95%.

12. The process of claim 1, wherein the first sample is (S)-3-(4-((4-(morpholinomethyl)benzyl)oxy)-1-oxoisoindolin-2-yl)piperidine-2,6-dione hydrochloride having an ee of 75%, the trituration occurs in methanol at 55° C., resulting in a second sample of (S)-3-(4-((4-(morpholinomethyl)benzyl)oxy)-1-oxoisoindolin-2-yl)piperidine-2,6-dione hydrochloride having an ee of 97.5%.

\* \* \* \* \*